United States Patent [19]

Failli et al.

[11] Patent Number: 5,071,988

[45] Date of Patent: Dec. 10, 1991

[54] SUBSTITUTED BENZOYLBENZENE-, BIPHENYL- AND 2-OXAZOLE-ALKANOIC ACID DERIVATIVES

[75] Inventors: Amedeo A. Failli, Princeton Junction, N.J.; Anthony F. Kreft, III, Langhorne; John H. Musser, Yardley, both of Pa.; Annette L. Banker, Plainsboro, N.J.; James A. Nelson, Washington Crossing, Pa.; Uresh S. Shah, Plainsboro, N.J.

[73] Assignee: American Home Products Corporation, New York, N.Y.

[21] Appl. No.: 661,734

[22] Filed: Feb. 27, 1991

Related U.S. Application Data

[63] Continuation-in-part of Ser. No. 427,677, Oct. 27, 1989.

[51] Int. Cl.$^5$ .................. C07D 215/14; C07D 413/10
[52] U.S. Cl. ..................................... 546/174; 546/172; 546/176; 514/311
[58] Field of Search ........................ 546/174, 172, 176

[56] References Cited

U.S. PATENT DOCUMENTS 3,641,127  2/1972  Farge et al. ........................ 260/516
3,969,402  7/1976  Adams et al. ................... 260/520 R
4,659,728  4/1987  Lewis et al. ......................... 514/374
4,681,940  7/1987  Musser et al. ........................ 546/174
4,876,346 10/1989  Musser et al. ........................ 546/174

FOREIGN PATENT DOCUMENTS 0339416 11/1989 European Pat. Off. ............ 546/174
0349062  1/1990 European Pat. Off. ............ 546/174

Primary Examiner—David B. Springer
Attorney, Agent, or Firm—George Tarnowski

[57] ABSTRACT

There are disclosed compounds of the formula

A(CH$_2$)$_n$O—B wherein
A is

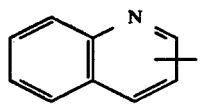

n is 1-2;
B is

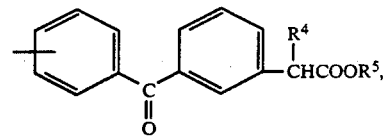

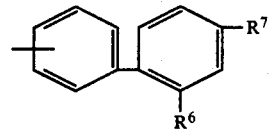

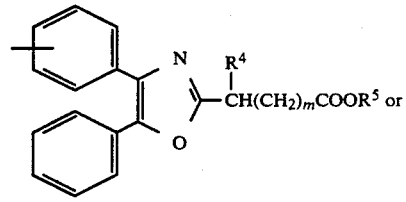

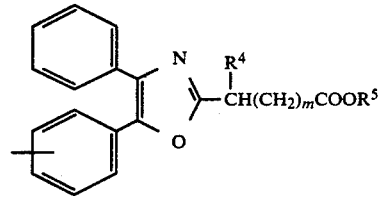

wherein
$R^4$ and $R^5$ are each, independently, hydrogen or lower alkyl;
$R^6$ is hydrogen, halo or nitro;

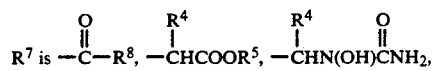

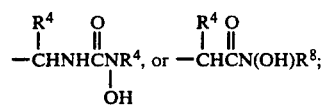

$R^8$ is lower alkyl;
m is 0-3;

and the pharmacologically acceptable salts thereof, and their use in the treatment of inflammatory conditions, such as rheumatoid arthritis, ulcerative colitis, psoriasis and other immediate hypersensitivity reactions; in the treatment of leukotriene-mediated nasobronchial obstructive air-passageway conditions, such as allergic rhinitis, allergic bronchial asthma and the like; and as gastric cytoprotective agents.

8 Claims, No Drawings

SUBSTITUTED BENZOYLBENZENE-, BIPHENYL- AND 2-OXAZOLE-ALKANOIC ACID DERIVATIVES

This is a continuation-in-part of U.S. Ser. No. 07/427,677, filed Oct. 27, 1989.

This invention relates to novel substituted benzoylbenzene-, biphenyl- and 2-oxazole-alkanoic acid derivatives possessing lipoxygenase inhibitory, phospholipase $A_2$ inhibitory and leukotriene antagonist activity, which are useful as anti-inflammatory, anti-allergic and cytoprotective agents.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides $PGG_2$ and $PGH_2$ by the cyclooxygenase pathway of arachidonic acid metabolism. These endoperoxides are also the precursors of the thromboxanes (Tx) $A_2$ and $B_2$. $TxA_2$ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin ($PGI_2$), which is a vasodilator with platelet aggregation inhibitory activity. In the event prostacyclin synthesis is impaired and/or platelet activation is enhanced, then thrombosis and vasoconstriction is favored. The role of prostanoids in haemostasis and thrombosis are reviewed by R. J. Gryglewski, *CRC Crit. Rev. Biochem.*, 7, 291 (1980) and J. B. Smith, *Am. J. Pathol.*, 99, 743 (1980). Cyclooxygenase metabolites are known to participate directly in the inflammatory response [see Higgs et al., Annals of Clinical Research, 16, 287-299 (1984)]. This is through their vasodepressor activities, participation in pain and fever augmentation of peptide mediator vascular permeability and edema forming properties. Finally, various aspects of cell mediated immunity are influenced by cyclooxygenase products.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., *J. Immun.*, 215, 115-118 (1980); *Biochem. Biophys. Res. Commun.*, 93, 1121-1126 (1980)].

The significance of these leukotrienes is that a great deal of evidence has been accumulated showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature*, 288, 484-486 (1980) and Piper, *Int. Arch. Appl. Immunol.*, 76, suppl. 1, 43 (1985)] which stimulate the release of mucus from airways in vitro [Marom et al., *Am. Rev. Resp. Dis.*, 126, 449 (1982)], are potent vasodilators in skin [see Bisgaard et al., *Prostaglandins*, 23, 797 (1982)], and produce a wheal and flare response [Camp et al., *Br. J. Pharmacol.*, 80, 497 (1983)]. The nonpeptide leukotriene, $LTB_4$, is a powerful chemotactic factor for leukocytes [see A. W. Ford-Hutchinson, *J. Roy. Soc. Med.*, 74, 831-833 (1981), which stimulates cell accumulation and affects vascular smooth muscle [see Bray, *Br. Med. Bull.*, 39, 249 (1983)]. The activity of leukotrienes as mediators of inflammation and hypersensitivity is extensively reviewed in Bailey and Casey, *Ann. Reports Med. Chem.*, 19, 87 (1986).

Phospholipase $A_2$ ($PLA_2$) is the critical rate limiting enzyme in the arachidonic acid (AA) cascade since it is responsible for the hydrolysis of esterified AA from the C-2 position of membrane phospholipids. This reaction generates two products (1) free AA which is then available for subsequent metabolism by either the cyclooxygenase or lipoxygenase enzymes and (2) lysophospholipid. When alkylarachidonoyl-glycerophosphatidylcholine is acted upon by the $PLA_2$ the generation of platelet activating factor (PAF) is initiated; PAF is pro-inflammatory in its own right [see Wedmore et al., *Br. J. Pharmacol.*, 74, 916-917 (1981)]. In this regard it may be noted that the anti-inflammatory steroids are thought to inhibit eicosanoid synthesis by inducing the synthesis of a $PLA_2$ inhibitory protein denominated macrocortin or lipomodulin [see Flower et al., *Nature, London*, 278, 456 (1979) and Hirata et al., *Proc. Natn. Acad. Sci. U.S.A.*, 77, 2533 (1980)].

As the initial step leading to subsequent conversion of AA to the various eicosanoids by the cyclooxygenase and lipoxygenase pathways, the $PLA_2$-mediated release of AA from membrane phospholipids is a critical event in attempting to deal with the various physiological manifestations which are based on the activity of the eicosanoids and/or PAF. Thus, while $PLA_2$ has been shown to be required for platelet aggregation [Pickett et al., *Biochem. J.*, 160, 405 (1976)], cardiac contraction and excitation [Geisler et al., *Pharm. Res. Commun.*, 9, 117 (1977)], as well as prostaglandin synthesis [Vogt, *Adv. Prostagl. Thromb. Res.*, 3, 89 (1978)], the inhibition of $PLA_2$ is indicated in the therapeutic treatment of both PAF induced or cyclooxygenase and/or lipoxygenase pathway product-mediated physiological conditions.

There is also evidence that products of the cyclooxygenase/lipoxygenase pathways play key roles in both the pathogenesis of gastric mucosal damage due to extracellular (gastric and intestinal contents, microorganisms, and the like) or intracellular (ischemia, viruses, etc.) agents, as well as in cytoprotection against such damage. Thus, on the one hand prostaglandins exert a cytoprotective effect on the gastric mucosa [see Robert, *Gastroenterology*, 77, 761-767 (1979)] and this action of the prostaglandins, especially of the E series, is considered to be of importance in the treatment of gastrointestinal ulceration [see Isselbacher, *Drugs*, 33 (suppl.), 38-46 (1987)]. On the other hand, ex vivo experiments have shown that gastric mucosal tissue from ethanol-pretreated rats is capable of $LTC_4$ generation and that this $LTC_4$ production is quantitatively related to the severity of the ethanol damage [see Lange et al., *Naunyn-Schmiedeberg's Arch. Pharmacol. Suppl.*, 330, R27, (1985)]. It has also been demonstrated that $LTC_4$ can induce vasoconstriction in both venous and arteriolar vessels in the rat submucosa [see Whittle, *IUPHAR Ninth Int. Cong. of Pharm.*, S30-2, London, England (1984)]. This is significant since ethanol-induced lesion formation in gastric mucosa may be multifactorial with, for example, stasis of gastric blood flow contributing significantly to the development of the hemorrhagic necrotic aspects of the tissue injury [see Guth et al., *Gastroenterology*, 87, 1083-90 (1984)]. Moreover, in the anesthetized cat, exogenous LTD$_4$ evokes both increased pepsin secretion and decreased transgastric potential [Pendleton et al., *Eur. J. Pharmacol.*, 125, 297-99 (1986)]. A particularly significant recent finding in this regard is that 5-lipoxygenase inhibitors and some leukotriene antagonists protect the gastric mucosa against lesions induced by the oral or parenteral administration of most nonsteroidal anti-inflammatory drugs [see Rainsford, *Agents and Actions*, 21, 316-319 (1987)]. Platelet activating factor (PAF) is also implicated as a mediator of gastrointestinal damage, and it has been recently shown that 5-lipoxygenase inhibitors inhibit PAF-induced gastric mucosal damage (*Gastroenterology*, 96, A55, A434, 1989). Accordingly, a significant body of evidence implicates the involvement of lipoxygenase products in the development of pathological features associated with gastric mucosal lesions, such as for example, those induced by ethanol exposure and administration of non-steroidal anti-inflammatory drugs. Thus, compounds which inhibit the biological effects of leukotrienes and PAF and/or which control the biosynthesis of these substances, as by inhibiting 5-lipoxygenase, are considered to be of value as cytoprotective agents.

Accordingly, the biological activity of the leukotrienes and SRS's, and of lipoxygenase as the enzyme leading to the metabolism of AA to leukotrienes, indicates that a rational approach to drug therapy to prevent, remove or ameliorate the symptoms of allergies, anaphylaxis, asthma and inflammation and for gastric cytoprotection must focus on either blocking the release of mediators of these conditions or antagonizing their effects. Thus, compounds which inhibit the biological effects of the leukotrienes and SRS's and/or which control the biosynthesis of these substances, as by inhibiting the PLA$_2$-mediated release of arachidonic acid from membrane phospholipids, or by inhibiting lipoxygenase, are considered to be of value in treating such conditions as allergic bronchial asthma, allergic rhinitis, as well as in other immediate hypersensitivity reactions and in providing gastric cytoprotection.

It has now been found that certain novel substituted benzoylbenzene-, biphenyl- and 2-oxazole-alkanoic acid derivatives inhibit PLA$_2$ and lipoxygenase, and antagonize products of the lipoxygenase pathway, and so are useful as anti-inflammatory, anti-allergic and cytoprotective agents. The present invention provides novel compounds having the following formula:

A(CH$_2$)$_n$O—B wherein
A is phenoxyethyl, phenoxyphenyl or a group having the formula

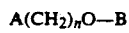

wherein
X is —N— or

Z is

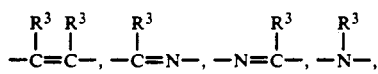

—S— or —O—;
R$^1$ is hydrogen, lower alkyl or phenyl;
R$^2$ is hydrogen or lower alkyl; or
R$^1$ and R$^2$ taken together form a benzene ring;
R$^3$ is hydrogen or lower alkyl;
n is 1-2;
B is

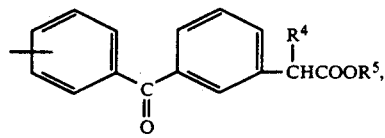

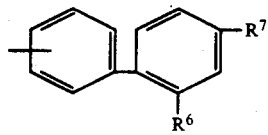

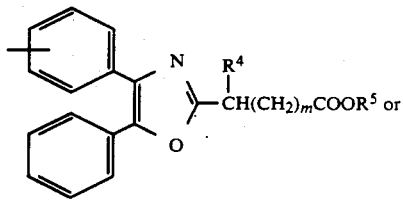

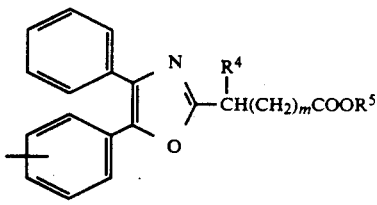

wherein
R$^4$ and R$^5$ are each, independently, hydrogen or lower alkyl;
R$^6$ is hydrogen, halo or nitro;

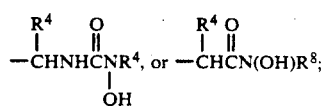

R$^8$ is lower alkyl;
m is 0-3;
and the pharmacologically acceptable salts thereof.

The term "lower alkyl" refers to moieties having 1-6 carbon atoms in the carbon chain. The term "halo" refers to fluoro, chloro or bromo.

The grouping A embraces, inter alia, 5- or 6-membered unsaturated nitrogen, sulfur or oxygen containing mono- or benzofused-heterocycles, optionally substituted with lower alkyl or phenyl. The foregoing definition embraces the following heterocyclic moieties: furyl, pyrrolyl, thienyl, oxazolyl, thiazolyl, imidazolyl, pyridyl, pyrazinyl, pyrimidinyl, benzofuranyl, benzothienyl, benzothiazolyl, indolyl, benzoxazolyl, quinolinyl, quinazolinyl, benzimidazolyl, quinoxalinyl, quinazolinyl and the like. Especially preferred are quinolinyl, benzothiazolyl, and benzimidazolyl.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic. The compounds which are carboxylic acids are capable of forming alkali metal and alkaline earth carboxylates and carboxylates of pharmacologically acceptable cations derived from ammonia or a basic amine. Examples of the latter include but are not limited to cations such as ammonium, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl-piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

The compounds of the invention can be prepared by the following reaction schemes. When it is desired to prepare compounds having the formula

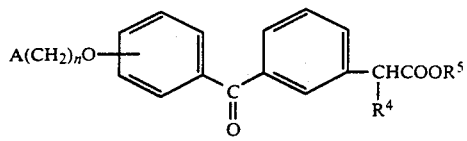

4-methoxybenzonitrile, for example, is reacted with 3-bromotoluene, followed by reaction with bromine in ethylene bromide to yield the intermediate 3-bromomethyl-[4'-methoxy]-benzophenone.

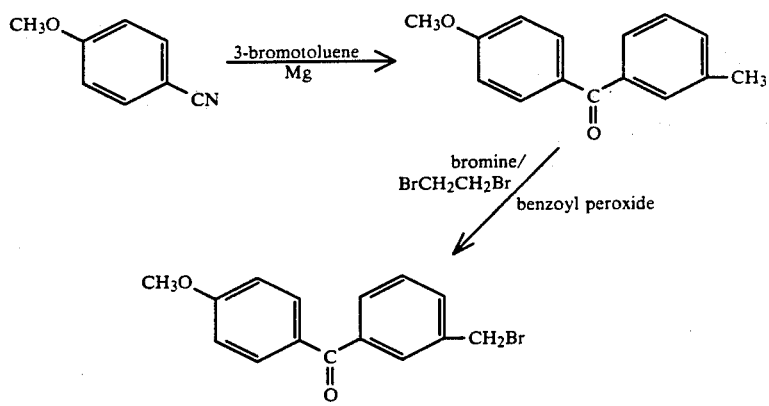

The bromo intermediate is reacted with sodium cyanide to yield the cyano intermediate, which is hydrolyzed in the presence of base to yield the carboxylic acid, which in turn is demethylated to yield the hydroxy carboxylic acid intermediate:

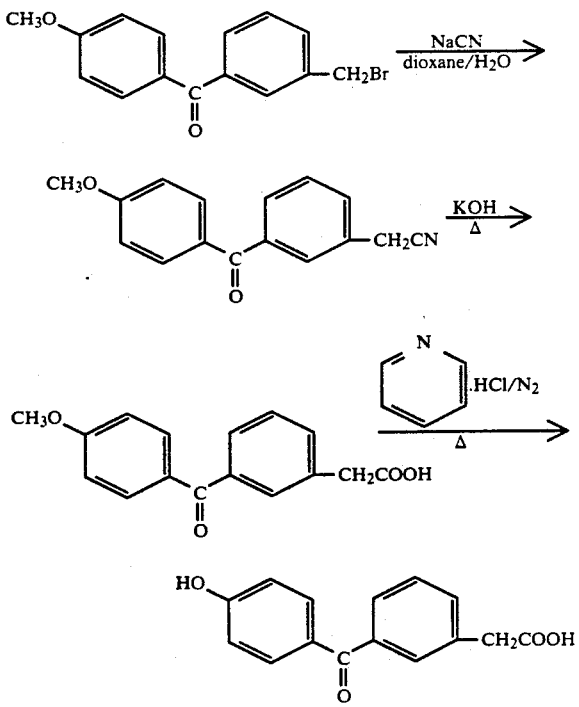

The hydroxy carboxylic acid intermediate is converted to the methyl ester with methanol in the presence of p-toluensulfonic acid followed by reaction with an appropriate haloalkyl-A compound, where A is as defined hereinbefore and hal is halo, to yield the desired final product as the methyl ester.

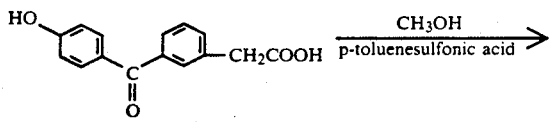

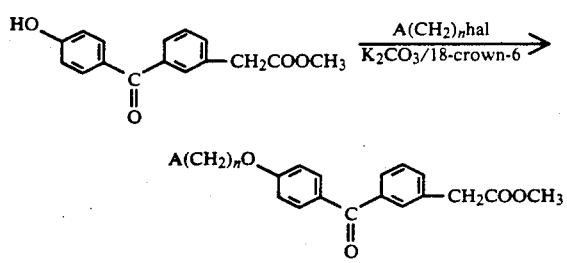

The ester can be hydrolyzed by conventional methods to yield the desired final product in free carboxylic acid form.

Compounds of the invention having the formula

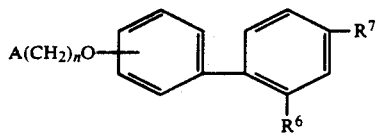

can be prepared by several routes. Compounds in which $R^6$ is nitro and $R^7$ is the

moiety can be prepared as follows; for example: 4-bromo-3-nitroacetophenone is reacted with 4-iodoanisole in the presence of copper bronze, to yield the intermediate methoxy-containing biphenyl, which is demethylated with aluminum bromide to yield the hydroxy intermediate. The latter is then reacted with an appropriate haloalkyl-A compound, where A is as defined hereinbefore and hal is halo, to yield the desired final product.

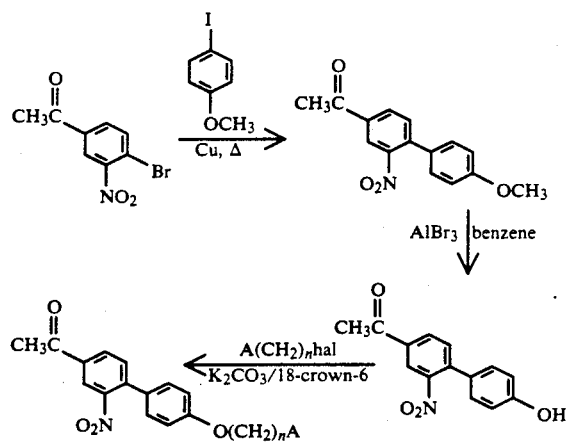

Compounds in which $R^6$ is halo and $R^7$ is the —CH-COOR$^5$ moiety can be prepared by a process which utilizes the 4-methoxy-biphenyl intermediate of the preceding scheme. Thus, the 4-acetyl-4-methoxy-2-nitrobiphenyl intermediate of the previous scheme is subjected to reduction with stannous chloride to yield the intermediate amino derivative, which is then subjected to replacement of the amino group with a halo group. For example, the amino group can be replaced with fluorine via a diazonium fluoroborate transitory intermediate prepared from the amino intermediate using sodium nitrite and tetrafluoroboric acid. The resulting acetyl-fluoro-methoxy biphenyl intermediate is converted to the corresponding carboxylic acid followed by demethylation with hydrogen bromide to yield the 2-fluoro-4'-hydroxy-[1,1'-biphenyl]-4-acetic acid intermediate:

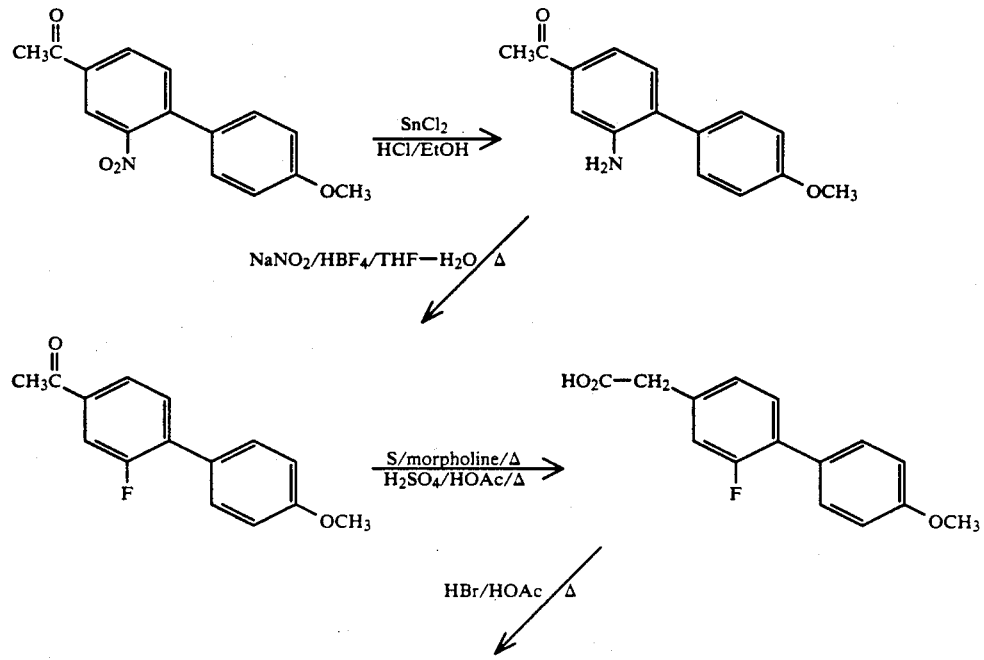

-continued

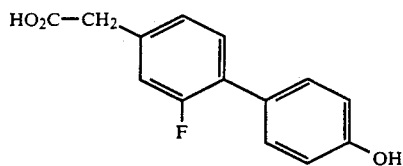

The latter carboxylic acid intermediate is esterified with methanol in the presence of p-toluenesulfonic acid and the latter is reacted with an appropriate haloalkyl-A compound, where A is as defined hereinbefore and hal is halo, to yield the desired final product as the methyl ester.

The ester can be hydrolyzed by conventional methods to yield the desired final product in its free carboxylic acid form.

Compounds in which $R^7$ is one of the nitrogen-containing moieties can be prepared from the carboxylic acid form of the above-discussed final products. Several possible sequences for these preparations are outlined below:

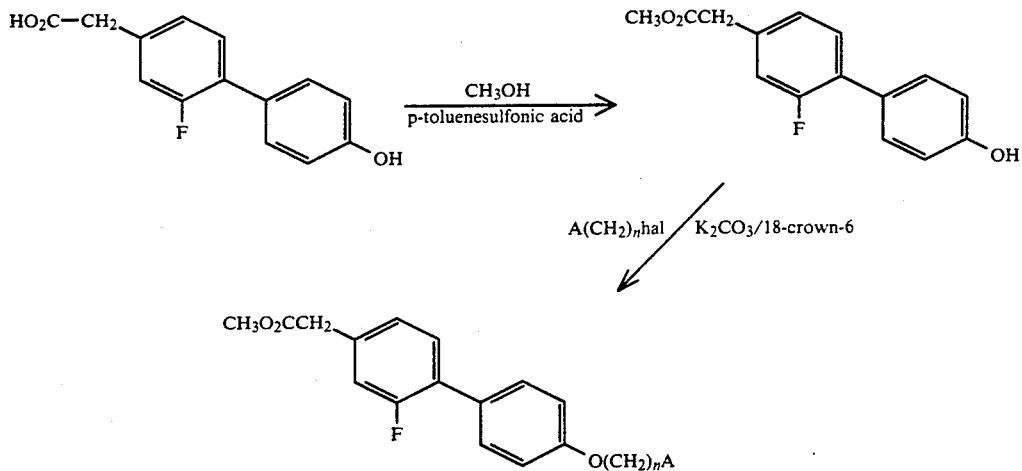

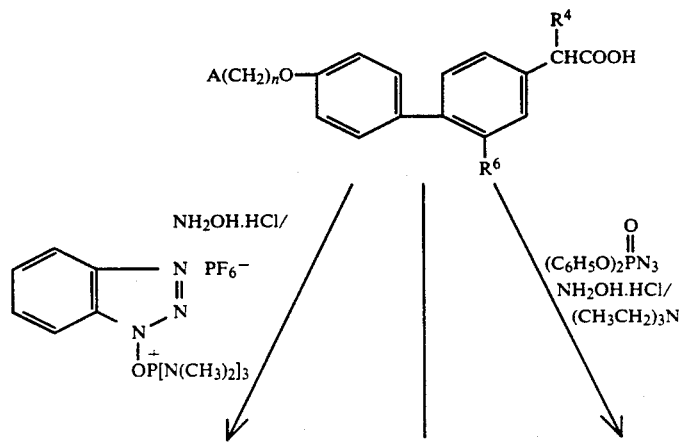

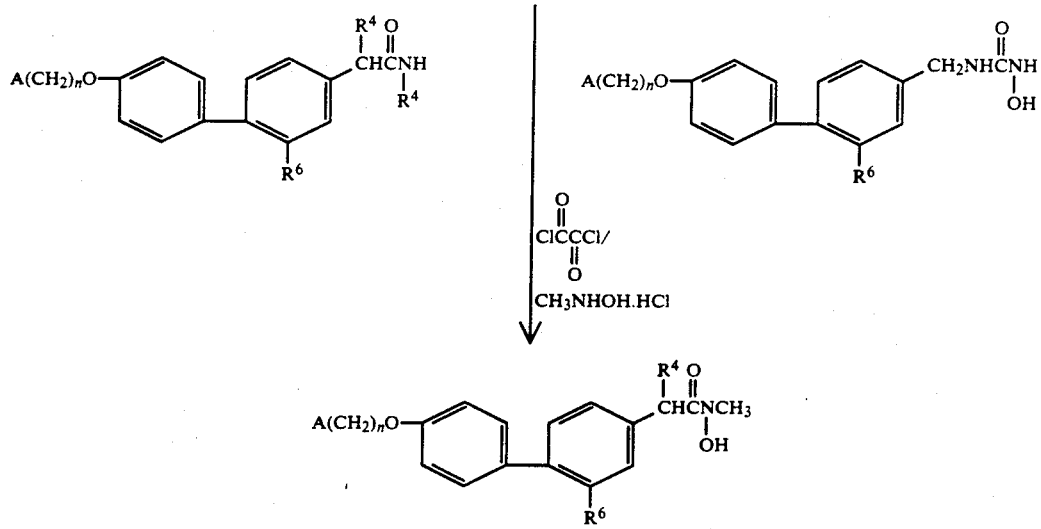

Compounds of the invention having the formula

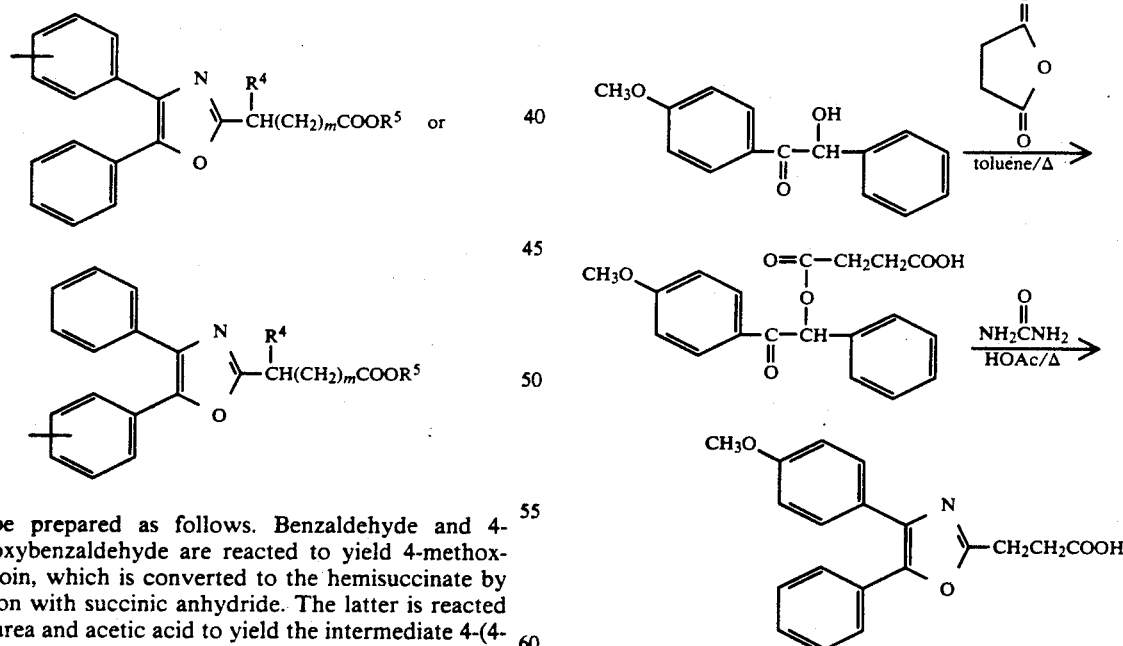

can be prepared as follows. Benzaldehyde and 4-methoxybenzaldehyde are reacted to yield 4-methoxybenzoin, which is converted to the hemisuccinate by reaction with succinic anhydride. The latter is reacted with urea and acetic acid to yield the intermediate 4-(4-methoxyphenyl)-5-phenyl-2-oxazole-propionic acid.

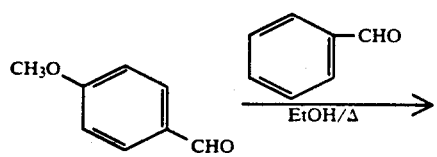

The latter intermediate is demethylated with hydrogen bromide and esterified with methanol to yield the corresponding hydroxy methyl ester intermediate, which is then reacted with an appropriate haloalky-A compound, where A is as defined hereinbefore and hal is halo, to yield the desired final product as the methyl ester.

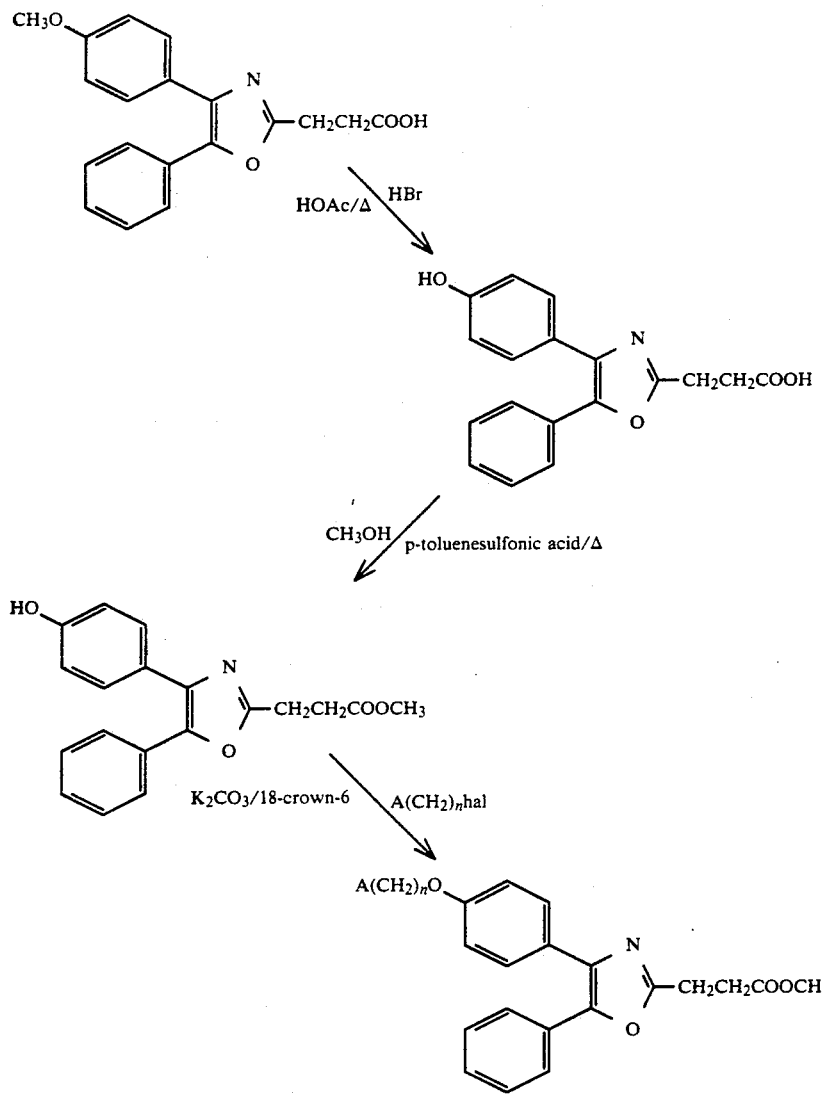

The ester can be hydrolyzed by conventional methods to yield the desired final product in its free carboxylic acid form.

The conventional starting materials used in the reaction sequences outlined above are available commercially or can be prepared by methods known in the art. Thus, for example, the intermediate compound 2-bromomethylquinoline can be prepared by the following reaction sequence:

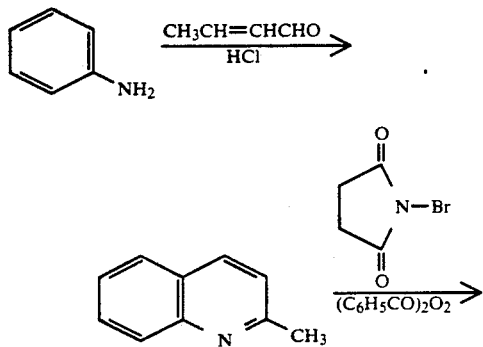

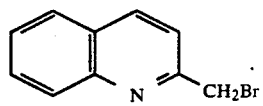

The benzo-fused heterocyclic compounds used in the above reaction sequences are also either commercially available or can be prepared by methods conventional in the art. Thus, for example, such intermediates as 1-methyl-2-chloromethylbenzimidazole, 2-chloromethylbenzthiazole and 2-chloromethylbenzoxazole can be prepared by the following reaction scheme

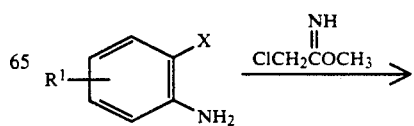

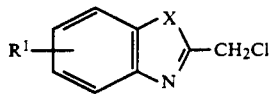

wherein X is O, S or NCH₃. The reaction is preferably carried out at a controlled low temperature in an organic solvent, such as methylene chloride.

The compounds of the invention, by virtue of their ability to inhibit the activity of PLA₂ enzyme, as well as that of lipoxygenase enzyme and to antagonize mediators arising from the enzymatic pathway, are useful in the treatment of conditions mediated by products of the oxidation of arachidonic acid. Accordingly, the compounds are indicated in the treatment of such diseases as rheumatoid arthritis, inflammatory bowel disease, osteoarthritis, tendinitis, bursitis, psoriasis (and related skin inflammation) and similar conditions involving inflammation. Moreover, by virtue of their ability to antagonize the effect of LTC₄, LTD₄ and LTE₄, which are the constituents of SRS-A, they are useful for the inhibition of symptoms induced by these leukotrienes. Accordingly, the compounds are indicated in the prevention and treatment of those disease states in which LTC₄, LTD₄ and LTE₄ are causative factors, for example allergic rhinitis, allergic bronchial asthma and other leukotriene mediated naso-bronchial obstructive air-passageway conditions, as well as in other immediate hypersensitivity reactions, such as allergic conjunctivitis. The compounds are especially valuable in the prevention and treatment of allergic bronchial asthma.

The compounds of the invention are cytoprotective agents and are considered especially useful when administered with conventional non-steroidal anti-inflammatory drugs, whose major side effect is gastrointestinal irritation. The cytoprotective effect of the compounds of the invention significantly reduces the gastroirritant impact of conventional anti-inflammatory drugs. This effect is based not only on the ability of the compounds of the invention to inhibit the biological effects of leukotrienes and/or control the biosynthesis of these substances, as by inhibiting lipoxygenase, but also by a shunting effect, whereby the control of the lipoxygenase pathway "shunts" the oxidation of arachidonic acid into the cyclooxygenase pathway, giving rise to an increase in the formation of cytoprotective prostaglandins. These biological effects make the compounds of the invention especially useful in treating such conditions as erosive esophagitis, inflammatory bowel disease and induced hemorrhagic lesions such as those induced by alcohol or non-steroidal anti-inflammatory drugs (NSAID's), hepatic ischemia, noxious agent induced damage or necrosis of hepatic, pancreatic, renal or myocardial tissue; liver parenchymal damage caused by hepatotoxic agents such as carbon tetrachloride and D-galactosamine; ischemic renal failure; disease-induced hepatic damage; bile salt-induced pancreatic or gastric damage; trauma or stress-induced cell damage; and glycerol-induced renal failure.

When the compounds of the invention are employed in the treatment of allergic airway disorders, as anti-inflammatory agents and/or as cytoprotective agents, they can be formulated into oral dosage forms such as tablets, capsules and the like. The compounds can be administered along or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The PLA₂ and lipoxygenase inhibitory and leukotriene antagonist effects, as well as the anti-inflammatory and potential gastroirritant effects of the compounds of the invention, may be demonstrated by standard pharmacological procedures which are described more full in the examples given hereinafter.

These procedures, inter alia, determine the specificity of action of the compounds of the invention as PLA₂ inhibitors as measured by their ability to inhibit the synthesis of LTB₄ and PGE₂ by rat glycogen-elicited polymorphonuclear leukocytes, as well as measure their ability to inhibit arachidonic acid release mediated by human source PLA₂. The pharmacological testing additionally demonstrates the ability of the compounds of the invention to inhibit, in vivo, the lipoxygenase and cyclooxygenase pathways of arachidonic acid metabolism.

The following examples show the preparation and pharmacological testing of compounds within the invention.

EXAMPLE 1

1-[2-Nitro-4'-(2-quinolinylmethoxy)-[1,1'-biphenyl]4-yl]ethanone

A. 4-Acetyl-4'-methoxy-2-nitro biphenyl

A stirred mixture of 4-iodoanisole (43.65 g, 0.187 mole), 4-bromo-3-nitro acetophenone (40.6 g, 0.166 mole) and copper powder (copper bronze, 36 g, 0.567 mole) kept under nitrogen is placed in an oil bath heated at 80° C. The temperature is slowly raised to 110° C. and the mixture is kept at this temperature for 5 days (TLC, 8:2 hexane-ethyl acetate). Upon cooling the mixture is dissolved in dichloromethane and filtered through a Celite pad. The filtrate and washings are evaporated and the residual thick, dark brown oil (58.4 g) is flash chromatographed (on silica Merck 60, preabsorbed in dichloromethane, eluted with 9:1 hexane-ethyl acetate to remove the impurities and 8:2 hexane-ethyl acetate to recover the main product) to provide 16.2 g (32%) of the title compound (yellow solid, m.p. 124°–126° C.).

NMR (CDCl$_3$, 400 MHz): δ2.67 (s, 3H, COCH$_3$), 3.85 (s, 3H, OCH$_3$), 6.97 (d, 2H, J 8.74 Hz, ArH), 7.27 (d, 2H, J 8.74 Hz, ArH), 7.56 (d, 1H, J 8 Hz, ArH), 8.15 (d, 1 H, J 8 Hz, ArH), 8.34 (s, 1H, ArH)

MS (EI, m/z): 271 (M)$^+$

B. 4-Acetyl-4'-hydroxy-2-nitro biphenyl

To a stirred solution of AlBr$_3$ (12.6 g, 47.4 mmole) in benzene (45 mL) is added dropwise under nitrogen a solution of the methylether (5 g, 18.45 mmole) of Step A in benzene (12 mL) over 30 minutes. The resulting solution is stirred at room temperature for 3.5 hours. (TLC, 8:2 hexane-ethyl acetate). The mixture is cooled in an ice bath and the complex is decomposed by the dropwise addition of 6N-HCl (ca. 37 mL). The organic layer is separated and the aqueous phase is reextracted with ether (3×). The combined extracts are concentrated to a small volume and extracted again with 2.5N-NaOH (2×50 mL+1×10 mL). The basic extracts are cooled and acidified with concentrated HCl (to pH 2). The solid is collected and dried (4.27 g, 90%). It is used in the next step without further purification.

NMR (CDCl$_3$, 400 MHz): δ2.67 (s, 3H, COCH$_3$), 5.03 (broad, 1H, OH), 6.91 (d, 2H, J 8.56 Hz, ArH), 7.23 (d, 2H, J 8.57 Hz, ArH), 7.55 (d, 1H, J 7.9 Hz, ArH), 8.15 (d, 1H, J 8.1 Hz, ArH), 8.34 (s, 1H, ArH).

MS (EI, m/z): 257 (b.p., M)$^+$

C. 1-[2-Nitro-4'(2-quinolinyl)[1,1'-biphenyl-4-yl]ethanone

A mixture of the phenol (4.4 g, 17.12 mmole) of Step B, powdered anhydrous potassium carbonate (2.37 g, 17.12 mmole), 18-crown-6 (0.453 g, 1.71 mmole) and acetonitrile (38 mL) is stirred at room temperature under nitrogen for 15 minutes. 2-Chloromethylquinoline (3.34 g, 18.83 mmole, free base freshly prepared from the hydrochloride salt) is added and the mixture is refluxed for 10 hours. (TLC, 7:3 hexane-ethyl acetate). A 10% excess of potassium carbonate, 18-crown-6 and the chloromethylquinoline is added and reflux continued for another 4 hours. The solvent is removed and the residue is diluted with water and extracted with ethyl acetate (3×). The extracts are washed and dried (MgSO$_4$). The residue is flash chromatographed (on silica Merck 60, preabsorbed in dichloromethane and eluted in order of increasing polarity with 7:3, 1:1 and 1:3 hexane-ethyl acetate followed by pure ethyl acetate) to provide the pure title compound (2.59 g). Recrystallization from toluene yields a yellow solid, m.p. 160°–162° C. (2.05 g, 30%).

NMR (CDCl$_3$, 400 MHz): δ2.66 (s, 3H, COCH$_3$), 5.43 (s, 2H, OCH$_2$Ar), 7.10 (d, 2H, J 8.7 Hz, ArH), 7.27 (d, 2H, J 8.7 Hz, ArH), 7.56 (m, 2H, ArH), 7.68 (d, 1H, J 8.49 Hz, ArH), 7.75 (dt, 1H, ArH), 7.84 (d, 1H, J 8.1 Hz, ArH), 8.09 (d, 1H, J 8.5 Hz, ArH), 8.14 (dd, 1H, ArH), 8.22 (d, 1H, J 8.49 Hz, ArH), 8.34 (s, 1H, ArH)

MS (EI, m/z): 398 (M)$^+$, 256, 158, 142 (b.p.)

Analysis for: C$_{24}$H$_{18}$N$_2$O$_4$. Calculated: C, 72.35; H, 4.55; N, 7.03. Found: C, 71.96; H, 4.75; N, 6.80.

EXAMPLE 2

2-Fluoro-4'-(2-quinolinylmethyoxy)-[1,1'-biphenyl]-4-acetic acid

A. 4-Acetyl-4'-methoxy-2-amino biphenyl

To a stirred, warm solution of tin (II) chloride (49.4 g, 218.9 mmole) in a mixture of concentrated HCl (72 mL) and ethanol (99 mL) is added over a period of 45 minutes the nitro derivative (10.7 g, 39.5 mmole) of Example 1A. The resulting yellow solution is refluxed for 3.5 hours (TLC, 1:1 hexane-ethyl acetate). The ethanol is removed and the residue is poured into a mixture of 50% NaOH (360 mL) and ice. The resulting solid is extracted (dichloromethane, 3×), the extracts are washed with water and dried (Na$_2$SO$_4$). Removal of the solvent provides a yellow solid (9.31 g, 97.8%), m.p. 152°–154° C.

NMR (CDCl$_3$, 400 MHz): δ2.59 (s, 3H, COCH$_3$), 380 (s, 3H, OCH$_3$), 6.97 (d, 2H, J 8.7 Hz, ArH), 7.23 (d, 1H, J 7.4 Hz, ArH), 7.40 (d, 2H, J 8.7 Hz, ArH), 7.48 (d, 1H, J 7.3 Hz, ArH), 7.49 (s, 1H, ArH).

MS (EI, m/z): 241 (b.p., M)$^+$, 226 (M-CH$_3$)$^+$, 198 (M-COCH$_3$)$^+$, 83.

B. 4-Acetyl-4'-methoxy-2-fluoro biphenyl

To a stirred, ice cold mixture of the aniline (9.2 g, 38.2 mmole) in tetrahydrofuran (26 mL), water (9.8 mL) and HBF$_4$ (48%, 35.1 mL) is slowly added a solution of sodium nitrite (2.82 g, 40.85 mmole) in water (5 mL). The internal temperature is kept below 5° C. during the addition. The mixture is then stirred for an additional 20 minutes at 0°–5° C. The diazonium fluoroborate is filtered off and washed with 10% HBF$_4$ and 10% methanol in ether and dried in vacuo. The salt is decomposed by heating at 70° C. in xylene (95 mL). When the decomposition subsides, the mixture is refluxed for another 2.5 hours (TLC, 1:1 hexane-ethyl acetate, UV). The xylene is removed and the residue is extracted with ethyl acetate (3×) and ether. The combined extracts are washed with 10% sodium carbonate and brine and dried (MgSO$_4$). Removal of the solvent provides an amber oil (6.03 g) which is purified by flash chromatography (on silica Merck 60, preabsorbed in dichloromethane and eluted with 95:5 hexane-ethyl acetate). The title compound is obtained as a yellow solid 3.12–4.75 g, (33–51% depending on the run); m.p. 100°–101° C.

NMR (CDCl$_3$, 400 MHz): δ2.62 (s, 3H, COCH$_3$), 3.86 (s, 3H, OCH$_3$), 7.00 (d, 2H, J 8.9 Hz, ArH), 7.50–7.80 (m, 5H, ArH).

MS (EI, m/z): 244 (M)$^+$, 229 (b.p., M-CH3)$^+$

C. 2-Fluoro-4'-methoxy-[1,1'-biphenyl]-4-acetic acid

A mixture of sulfur (0.468 g, 14.6 mmole), morpholine (2.57 mL) and the ketone (3.95 g, 16.2 mmole) of Step A is refluxed for 17 hours (TLC, acid treated silica plate, 8:2 hexane-ethyl acetate). Upon cooling, glacial acetic acid (9.9 mL), sulfuric acid (1.6 mL) and water (4 mL) are added and the reflux resumed for 30 hours. Water is then added and the mixture is extracted with ether (3×). The combined extracts are concentrated to a smaller volume and extracted with 10% sodium carbonate. The basic extracts are carefully acidified in the cold with concentrated HCl (to pH 2). The title acid is extracted with ether (3×) and the extracts are washed and dried (MgSO$_4$). Removal of the solvent provides a tan to brown solid (2.37 g, 56.3%) melting at 140°–142° C.

NMR (CDCl$_3$, 400 MHz): δ3.68 (s, 2H, CH$_2$COO), 3.85 (s, 3H, OCH$_3$), 6.96-7.50 (m, 7H, ArH).

MS (EI, m/z): 260 (M)$^+$, 215 (b.p., M-COOH)$^+$.

D. 2-Fluoro-4'-hydroxy-[1,1'-biphenyl]-4-acetic acid

To a solution of the methylether (1.31 g, 5.04 mmole) of Step C in glacial acetic acid (17 mL) is added dropwise 48% HBr in acetic acid (25 mL) and the mixture is refluxed for 4.5 hours (TLC, 7:3 hexane-ethyl acetate). A little water is added and the mixture is extracted with ether (3×). The extracts are washed and dried (MgSO$_4$). Removal of the solvent provides the title compound as a tan solid (1.13 g, 92%), m.p. 208°-210° C.

NMR (DMSO-d$_6$, 400 MHz): δ3.61 (s, 2H, CH$_2$COO), 6.83 (d, 2H, J 8.64 Hz, ArH), 7.1-7.42 (m, 5H, ArH), 9.61 (s, 1H, COOH).

MS (C I, m/z): 246 (M)$^+$, 201 (b.p., M-COOH)$^+$.

E. 2-Fluoro-4'-hydroxy-[1,1'-biphenyl]-4-acetic acid methylester

A solution of the acid (1.1 g, 4.47 mmole) of Step D in methanol (10 mL) containing p-toluenesulfonic acid .H$_2$O (0.159 g) is refluxed for 1.5 hours (TLC, acid treated silica plate, hexane-ethyl acetate 7:3). The solvent is removed, the residue is dissolved in ethyl acetate, washed with brine and dried (MgSO$_4$). The tan solid (1.16 g, m.p. 115°-118° C., quantitative yield) is used as such in the next step.

NMR (CDCl$_3$, 400 MHz): δ3.65 (s, 2H, CH$_2$COO), 3.73 (s, 3H, COOCH$_3$), 6.88 (d, 2H, J 8.8 Hz, ArH), 7.10 (m, 2H, ArH), 7.32-7.44 (m, 3H, ArH).

MS (EI, m/z): 260 (M)$^+$, 201 (b.p., M-COOCH$_3$)$^+$.

F. 2-Fluoro-4'-(2-quinolinylmethoxy)-[1,1'-biphenyl]-4-acetic acid methylester

A stirred mixture of the phenol (1.16 g, 4.46 mmole) of Step E, powdered anhydrous potassium carbonate (0.616 g, 4.46 mmole), 18-crown-6 (0.118 g, 0.445 mmole) and acetonitrile (10 mL) is stirred at room temperature under nitrogen for 15 minutes. 2-Chloromethylquinoline (0.871 g, 4.9 mmole, free base freshly prepared from the hydrochloride salt) is then added and the mixture is placed in an oil bath heated at 65° C. for 5 hours. A 10% excess of potassium carbonate, 18-crown-6 and the chloromethylquinoline is added and the heating continued for another 6 hours (TLC, 19:1 dichloromethane-methanol or 7:3 hexane-ethyl acetate). The solvent is removed and the residue is diluted with water and extracted with ethyl acetate (3×). The extracts are washed and dried (MgSO$_4$). Removal of the solvent provides a tan solid which is purified by flash chromatography (on silica Merck 60, preabsorbed with dichloromethane, eluted with 7:3 hexane-ethyl acetate). The title compound thus obtained (1.55 g, 87%) is recrystallized from methanol. The off-white solid melts at 99°-101° C.

NMR (CDCl$_3$, 400 MHz): δ3.64 (s, 2H, CH$_2$COO), 3.72 (s, 3H, COOCH$_3$), 5.43 (s, 2H, OCH$_2$Ar), 7.1 (m, 4H, ArH), 7.35 (t, 1H, ArH), 7.47 (d, 2H, ArH), 7.55 (t, 1H, ArH), 7.69 (d, 1H, ArH), 7.74 (t, 1H, ArH), 7.84 (d, 1H, ArH), 8.09 (d, 1H, ArH), 8.20 (d, 1H, ArH).

MS (EI, m/z): 401 (M)$^+$, 142, 114 (b.p.)

Analysis for: C$_{25}$H$_{20}$FNO$_3$. Calculated: C, 74.80; H, 5.02; N, 3.49. Found: C, 74.68; H, 4.65; N, 3.49.

G. 2-Fluoro-4'-(2-quinolinylmethoxy)-[1,1'-biphenyl]-4-acetic acid

A solution of the ester (1.69 g, 4.21 mmole) of Step F, in dry tetrahydrofuran (20 mL) is treated dropwise under nitrogen with 1N-LiOH (12.6 mL) and the mixture is stirred for 3 hours at room temperature (TLC, 19:1 dichloromethane-methanol or 1:1 hexane-ethyl acetate). The solvent is removed, the residue is treated with water and neutralized (to pH 6.5) with 10% acetic acid. The acid is extracted with ethyl acetate (large volume needed) and the extracts are dried (MgSO$_4$) and evaporated to dryness to yield an off-white solid (1.65 g, quantitative yield, m.p. 190°-193° C., dec.). Recrystallization from ethyl acetate provides a white solid (1.32 g, 80%, m.p. 195°-196° C. dec.). The analytical sample is dried in vacuo at 40° C.

NMR (DMSO-d$_6$, 400 MHz): δ3.62 (s, 2H, CH$_2$COO), 5.41 (s, 2H, CH$_2$OAr), 7.15 (m, 4H, ArH), 7.41 (t, 1H, J 8 Hz, ArH), 7.48 (d, 2H, ArH), 7.61 (t, 1H, ArH), 7.69 (d, 1H, ArH), 7.78 (dt, 1H, ArH), 8.01 (m, 2H, ArH), 8.42 (d, 1H, ArH), 12.42 (s, COOH).

MS (+FAB, m/z): 388 (M)$^+$.

Analysis for: C$_{24}$H$_{18}$FNO$_3$. Calculated: C, 74.41; H, 4.68; N, 3.62. Found: C, 74.28; H, 4.48; H, 3.69.

EXAMPLE 3

3-[4-(2-Quinolinylmethoxy)benzoyl]benzene acetic acid

A. 3-Methyl-[4'-methoxy]-benzophenone

A 3-neck flask equipped with a condenser, mechanical stirrer and dropping funnel is charged under nitrogen with 1.925 g (79.19 g.a.) of magnesium turnings and enough ether to cover the turnings. A few drops of a solution of 3-bromotoluene (15.79 g, 92.28 mmole) in ether (40 mL) is then added along with a crystal of iodine to initiate the reaction. The remainder of the solution is then added dropwise and the mixture is refluxed until most of the magnesium has disappeared. After cooling, a solution of 4-methoxybenzonitrile (10 g, 75.1 mmole, dried in vacuo over P$_2$O$_5$) is added in one portion. The mixture is refluxed for 2 hours (TLC, no starting material present), cooled (ice bath) and slowly treated with cold water (130 mL) followed by dilute H$_2$SO$_4$ (1:1, v/v, 25 mL). The decomposition of the complex is completed by refluxing the mixture for 4 hours (followed by TLC, 8:2 ether-ethyl acetate). Following stirring overnight at room temperature, the layers are separated and extracted with ether (3×). The extracts are washed with 5% NaHCO$_3$, dried (MgSO$_4$) and evaporated to dryness. The crude material (amber oil, 13.93 g) is purified by flash chromatography (on silica Merck-60, eluted with 8:2 petrolether-ethyl acetate) to provide the title compound as a light yellow oil (12.5 g, 73.5%).

NMR (CDCl$_3$, 400 MHz): δ2.4 (s, 3H, CH$_3$), 3.9 (s, 3H, OCH$_3$), 6.96 (d, J 8.8 Hz, 2H, ArH), 7.38 (m, 2H, ArH), 7.53 (d, J 6.9 Hz,1H, ArH), 7.57 (s, 1H, ArH), 7.82 (d, J 8.7 Hz,2H, ArH).

MS (EI, m/z): 226 (M)$^+$, 135 (b.p.), 91.

B. 3-Bromomethyl-[4'-methoxy]-benzophenone

A solution of the benzophenone (17.5 g, 77.4 mmole) of Step A in ethylene bromide (26.5 mL) (containing a small amount of benzoyl peroxide) is heated at reflux. A solution of bromine (12.7 g, 79.6 mmole) in ethylene bromide (15 mL) is added dropwise over 30 minutes while the mixture is irradiated with a Photolamp (300 W). Reflux is continued for 17 hours (TLC, 9:1 petrolether-ethylacetate, traces of starting material still present). The solvent is removed in vacuo and the residue (brown oil, 39.22 g) is purified by flash chromatography (on silica Merck-60, preabsorbed in dichloromethane, eluted with 9:1 petrolether-ethyl acetate) to give unreacted starting material (2.59 g, ca. 15%) along with the desired product (14.36 g, 61% or 71.5% based on recovered unreacted starting material) and some mixed fractions (ca. 5.20 g). The light yellow solid melts at 58°–61° C. and it is used as such in the next step.

NMR (CDCl$_3$, 400 MHz): δ3.88 (s, 3H, OCH$_3$), 4.52 (s, 2H, CH$_2$Br), 6.96 (d, J 8.8 Hz, 2H, ArH) 7.44 (t, J 7.6 Hz, 1H, ArH), 7.58 (d, J 7.8 Hz, 1H, ArH), 7.66 (d, J 7.6 Hz, 1H, ArH), 7.76 (s, 1H, ArH), 7.81 (d, J 8.8 Hz, 1H, ArH).

MS (EI, m/z): 306/304 (1 bromine, M)+, 225, 135 (b.p.). Trace of dibromo at 386/384/382 (possibly

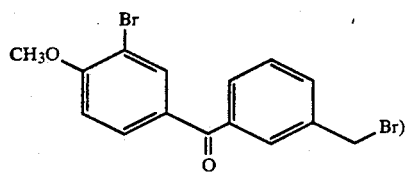

C. 3-Cyanomethyl-[4'-methoxy]-benzophenone

The bromo compound (14 g, 45.9 mmole) of Step B, is dissolved in dioxane (30 mL) and a solution of NaCN (7 g) in water (28.5 mL) is added. The mixture is refluxed for 6 hours (TLC, petrolether-ethyl acetate 8:2), charcoalized if needed and extracted with ether (3×). The extracts are dried (MgSO$_4$) and evaporated to dryness to yield a brown oil (13.44 g). The crude product is purified by flash chromatography (on silica Merck-60, pre-absorbed in dichloromethane, eluted with 6:4 hexane-ethyl acetate) to provide the pure product (10.69 g, 92%) as a light yellow oil that sets up upon standing. The nearly colorless solid melts at 70°–71° C.

NMR (CDCl$_3$, 400 MHz): δ3.80 (s, 2H, CH$_2$CN), 3.87 (s, 3H, OCH$_3$), 6.95 (d, J 8.6 Hz, 2H, ArH), 7.48 (t, J 7.7 Hz, 1H, ArH), 7.54 (d, J 7.6 Hz, 1H, ArH), 7.68 (s+d, J 7.6 Hz, 2H, ArH), 7.79 (d, J 8.6 Hz, 2H, ArH).

MS (EI, m/z): 251 (M)+, 135 (b.p.).

D. 3-[4-Methoxybenzoyl]-phenylacetic acid

The nitrile (4 g, 15.9 mmole) of Step C, is dissolved in 40% NaOH (40 mL) and the solution is heated at reflux under nitrogen for 7 hours (TLC, toluene-methanol 9:1). Water is added while cooling in an ice bath. The solution is washed with ethyl acetate and then acidified in the cold with concentrated HCl (to pH 2). The acid is extracted with ethyl acetate (3×) and the extracts are dried (MgSO$_4$) and evaporated to dryness to yield the crude product (yellow solid, 3.56 g, 82%), m.p. 138°–140° C.

NMR (CDCl$_3$, 400 MHz): δ3.72 (s, 2H, CH$_2$COO), 3.88 (s, 3H, OCH$_3$), 6.95 (d, J 8.8 Hz, 2H, ArH), 7.43 (t, 1H, ArH), 7.48 (d, 1H, ArH), 7.65 (d, 1H, ArH), 7.68 (s, 1H, ArH), 7.81 (d, J 8.6 Hz, 2H, ArH).

MS (EI, m/z): 270 (M)+, 211 (M-CH$_2$COOH)+, 135 (b.p.), 107.

E. 3-[4-Hydroxybenzoyl]-phenylacetic acid

An intimate mixture of the acid (8.1 g, 0.030 mole) of Step D, and pyridine hydrochloride (13.87 g, 0.120 mole) is stirred under nitrogen in an oil bath heated at 200°–210° C. for 7 hours (TLC, toluene-methanol 9:1, dichloromethane-methanol 9:1). After cooling, the mixture is dissolved in dichloromethane. The solution is extracted with 1N-NaOH, the extract acidified in the cold with concentrated HCl and extracted with ethyl acetate (3×). After drying (MgSO$_4$) the solvent is removed to provide the crude title compound as a tan solid (7.61 g, quantitative yield), m.p. 147°–149° C.

NMR (DMSO-d$_6$, 400 MHz): δ3.67 (s, 2H, CH$_2$COO), 6.88 (d, J 8.84 Hz, 2H, ArH), ca. 7.5 (m, 4H, ArH), 7.65 (d, J 8.8 Hz, 2H, ArH), 10.4 (s, 1H, OH), ca. 12.3 (s, 1H, COOH).

MS (m/z): 257 (M+H)+, 217, 131, 91 (b.p.).

F. 3-[4-Hydroxybenzoyl]-phenylacetic acid methylester

A mixture of the acid (8.56 g, 33.4 mmole) of Step E and p-toluenesulfonic acid monohydrate (1.05 g, 5.6 mmole) in methanol (70 mL) is refluxed for 2.5 hours (TLC, methanol-toluene 1:9). The methanol is evaporated and the residue is dissolved in ethyl acetate and washed with brine. After drying (MgSO$_4$) the solvent is removed to yield a tan solid (8.68 g, 96.2%, m.p. 111°–113° C.). The crude product is used as such in the next step.

NMR (CDCl$_3$, 400 MHz): δ3.69 (s, 2H, CH$_2$COO), 3.69 (s, 3H, COOCH$_3$), 6.86 (d, J 8.4 Hz, 2H, ArH), 7.41 (t, 1H, 7.58 Hz, 1H, ArH), 7.47 (d, J 7.56 Hz, 1H, ArH), 7.62 (d, J 7.4 Hz, 1H, ArH), 7.64 (s, 1H, ArH), 7.74 (d, 2H, J 8.4 Hz, ArH).

MS (m/z): 271 (M+H)+, 217, 131, 91 (b.p.).

G. 3-[4-(2-Quinolinylmethoxy)benzoyl]benzene acetic acid methylester

A mixture of the phenol (4 g, 14.8 mmole) of Step F, powdered anhydrous K$_2$CO$_3$ (2.05 g, 14.8 mmole) and 18-crown-6 (0.4 g, 1.48 mmole) in acetonitrile (35 mL) is stirred at room temperature under nitrogen for 15 minutes. 2-Chloromethylquinoline (2.9 g, 16.28 mmole, freshly prepared from the hydrochloride salt) is added in one portion and the mixture is heated in an oil bath kept at 65°–70° C. for 8 hours (TLC, toluene-methanol 9:1). A 10% excess of K$_2$CO$_3$, crown ether and chloromethylquinoline is added and the heating is continued for another 8 hours. The acetonitrile is evaporated and the residue is partitioned between water and ethyl acetate. The organic layer is dried (MgSO$_4$) and evaporated to yield a tan solid (6.57 g). The crude product is purified by flash chromatography (on silica Merck-60, preabsorbed in dichloromethane, eluted with petrolether-ethyl acetate 7:3) to give the title compound as a light yellow solid (5.03 g, 82.7%) m.p. 93°–95° C.

NMR (CDCl$_3$, 400 MHz): δ3.67 (s, 5H, CH$_2$COO+OCH$_3$), 5.45 (s, 2H, ArCH$_2$O), 7.08 (d, J 8.8 Hz, 2H, ArH), 7.40 (t, J 7.8 Hz, 1H, ArH), 7.46 (d, J 7.7 Hz, 1H, ArH), 7.55 (t, J 7.3 Hz, 1H, ArH), 7.6–7.66 (m, 3H, ArH), 7.7–7.82 (m, 4H, ArH), 8.07 (d, 1H, ArH), 8.20 (d, J 8.4 Hz, 1H, ArH).

MS (EI, m/z): 411 (M)+, 142, 121 (b.p.).

H. 3-[4-(2-Quinolinylmethoxy)benzoyl]benzene acetic acid

To a solution of the ester (5 g, 12.16 mmole) of Step G, in dry tetrahydrofuran (66 mL) is added 1N-LiOH (37 mL, 37 mmole) and the mixture is stirred under nitrogen at room temperature for 2.5 hours (TLC, toluene-MeOH 9:1). The tetrahydrofuran is evaporated and the residue is diluted with water, acidified (to pH 6.5) with 10% acetic acid and extracted with ethyl acetate (3×). The extracts are washed with brine, dried (MgSO$_4$) and evaporated to dryness. The crude product (4.94 g, pale yellow solid) is recrystallized from ethyl acetate to provide 3.65 g (75%) of the pure title compound (white solid, m.p. 146°–147° C.).

NMR (DMSO-d$_6$, 400 MHz): δ3.68 (s, 2H, CH$_2$COO), 5.48 (s, 2H, ArCH$_2$O), 7.22 (d, 2H, J 8.8 Hz, ArH), 7.47 (m, 1H, ArH), 7.53 (m, 2H, ArH), 7.62 (m, 2H, ArH), 7.69 (d, J 8.4 Hz, 1H, ArH) 7.74–7.82 (m, 3H, ArH), 8.2 (m, 2H, ArH), 8.43 (d, J 8.5 Hz, 1H, ArH), 12.39 (1H, COOH).

MS (EI, m/z): 397 (b.p., M)$^+$, 380 (M-OH)$^+$, 142.

Analysis for: C$_{25}$H$_{19}$NO$_4$. Calculated: C, 75.57; H, 4.78; N, 3.53. Found: C, 75.22; H, 4.76; N, 3.39.

EXAMPLE 4

3-[4-(2-Naphthalenylmethoxy)benzoyl]benzene acetic acid

A. 3-[4-(2-Naphthalenylmethoxy)benzoyl]benzene acetic acid methylester

A mixture of the phenol (1 g, 3.7 mmole) of Example 3F, powdered anhydrous K$_2$CO$_3$ (0.48 g, 3.7 mmole), 18-crown-6 (0.098 g, 0.37 mmole) and acetonitrile (10 mL) is stirred under nitrogen for 15 minutes. 2-Bromomethylnaphthalene (0.496 g, 4.07 mmole) is added and the mixture is placed in an oil bath heated at 65°–70° C. for 10 hours (TLC, dichloromethane-ethyl acetate 8:2). A 10% excess of K$_2$CO$_3$, crown ether and bromomethylnaphthalene is added and the heating is continued for another 4 hours. The acetonitrile is evaporated and the residue dissolved in water and extracted with ethyl acetate (3×). The extracts are washed with 1N-NaOH and brine, dried (MgSO$_4$) and evaporated to dryness. The crude product (1.49 g, waxy solid) is used as such in the next step.

NMR (CDCl$_3$, 400 MHz): δ3.7 (s, 5H, OCH$_3$+CH$_2$COO), 5.32 (s, 2H, ArCH$_2$O), 7.08 (d, J 8.7 Hz, 2H, ArH), 7.4–7.56 (m, 5H, ArH), 7.63–7.68 (m, 2H, ArH), 7.82–7.92 (m, 6H, ArH).

MS (m/z): 410 (M)$^+$, 141 (b.p.).

B. 3-[4-(2-Naphthalenylmethoxy)benzoyl]benzene acetic acid

A solution of the ester (1.29 g, 3.15 mmole) of Step A, is treated dropwise with 1N-LiOH and the mixture is stirred under nitrogen overnight. The solvent is evaporated and the residue is dissolved in water, acidified in the cold with 10% acetic acid (to pH 3) and extracted with ethyl acetate (3×). The extracts are dried (MgSO$_4$) and evaporated to dryness. The residue (1.24 g, quantitative yield) is recrystallized by dissolving it in a relatively large volume of warm ethyl acetate-dichloromethane followed by concentrating to half volume. The precipitate is collected and dried at 45° C. in vacuo (0.610 g, 48.8%), m.p. 150°–152° C.

NMR (DMSO-d$_6$, 400 MHz): δ3.70 (s, 2H, CH$_2$COO), 5.40 (s, 2H, ArCH$_2$), 7.20 (d, 2H, ArH), 7.45–7.60 (m, 7H, ArH), 7.75 (d, 2H, ArH), 7.95 (m, 3H, ArH), 8.02 (s, 1H, ArH), 12.47 (broad s, 1H, COOH).

MS (+FAB, m/z): 397 (M+H)$^+$, 217, 141.

Analysis for: C$_{26}$H$_{20}$O$_4$. Calculated: C, 78.78; H, 5.09. Found: C, 78.12; H, 5.13.

EXAMPLE 5

5-Phenyl-4-[4-(2-Quinolinylmethoxy)phenyl]-2-oxazole propanoic acid

A. 4-Methoxybenzoin

To a solution of KCN (5 g) in water (35 mL) is added 4-methoxybenzaldehyde (27.2 g, 0.2 mole), benzaldehyde (21.2 g, 0.2 mole) and 95% ethanol (70 mL). The mixture is refluxed under nitrogen for 4.5 hours and the ethanol removed in vacuo. Water (200 mL) is added to the residue and then distilled off at reduced pressure (to remove remaining unreacted bezaldehyde). The procedure is repeated twice and the residual water azeotroped with ethanol. The crude product (56.3 g, orange semi-solid) is purified by flash-chromatography (on silica Merck-60, preabsorbed in dichloromethane-ethyl acetate and eluted with hexane-ethyl acetate 8:2) to yield a light yellow solid (20.1 g, 41.5%), m.p. 99°–101° C.

NMR (CDCl$_3$, 400 MHz): δ3.82 (s, 3H, OCH$_3$), 4.62 (broad s, 1H, OH), 5.88 (s, 1H, CHOH), 6.86 (d, 2H, J 8.94 Hz, ArH), 7.22–7.38 (m, 5H, ArH), 7.91 (d, 2H, J 8.94 Hz, ArH).

MS (CI, m/z): 243 (b.p., M+H)$^+$, 225, 197, 137 (M-PhCO)$^+$.

B. 4-Methoxybenzoin hemisuccinate

A mixture of 4-methoxybenzoin (20 g, 0.083 mole) and succinic anhydride (9.1 g, 0.091 mole) in toluene (6 mL) is heated for 7 hours under nitrogen at 135° C. (internal temp.). The solution is poured into 0.5N-NaHCO$_3$, the organic layer was separated and reextracted with 0.5N-NaHCO$_3$. The combined extracts are washed with ether and then acidified in the cold with concentrated HCl. The liberated oil is extracted with ethyl acetate (3×), the extracts washed with water and dried (MgSO$_4$). Removal of the solvent yields a yellow solid (20.89 g, 73.8%), m.p. 104°–108° C. It is used in the next step without further purification.

NMR (CDCl$_3$, 400 MHz): δ2.72–2.82 (mm, 4H, CH$_2$CH$_2$COO), 3.82 (s, 3H, OCH$_3$), 6.86 (d, 2H, J 9.1 Hz, ArH), 7.34–7.46 (m, 5H, ArH), 7.92 (d, 2H, J 9.1 Hz, ArH).

MS (EI. m/z): 342 (M)$^+$, 135 (b.p.).

C. 4-(4-Methoxyphenyl)-5-phenyl-2-oxazole-propanoic acid

A mixture of the crude 4-methoxybenzoin hemisuccinate (20.8 g, 0.061 mole) of Step B, urea (8.7 g, 0.146 mole) and acetic acid (60 mL) is heated at reflux under nitrogen for 5.5 hours. The mixture is cooled and poured into ice water. The liberated oil is extracted with ethyl acetate (3×). The extracts are washed with water until neutral and then extracted with saturated sodium carbonate. The combined aqueous extracts are carefully acidified in the cold with concentrated HCl and extracted with ethyl acetate. The organic extract is dried (MgSO$_4$) and evaporated to dryness to provide a waxy yellow oil (19.6 g). Purification of the residue by flash chromatography (on silica Merck-60, eluant: dichloromethane-ethyl acetate 8:2) yields a pale yellow solid (14.3 g, 72.7%), m.p. 100°–101° C.

NMR (CDCl$_3$, 400 MHz): δ2.96 (t, 2H, CH$_2$C), 3.20 (t, 2H, CH$_2$COO), 3.83 (s, 3H, OCH$_3$), 6.90 (d, 2H, ArH), 7.28–7.38 (m, 3H, ArH), 7.54–7.62 (m, 4H, ArH).

MS (EI, m/z): 323 (M)$^+$, 278 (b.p., M-COOH)$^+$, 152, 77.

D. 4-(4-Hydroxyphenyl)-5-phenyl-2-oxazole-propanoic acid

To a solution of the methoxy acid (5.6 g, 17.3 mmole) of Step C, in acetic acid (55 mL) is added 48% HBr (84 mL) and the mixture is heated at reflux under nitrogen for 8 hours (TLC, 1:1 hexane-ethyl acetate). After cooling, water is added and the solution extracted with ethyl acetate (3×). The extract is dried (MgSO$_4$) and evaporated to dryness. The residue (brown waxy oil, 5.25 g, 99%) is used in the next step without further purification. For analytical characterization a small sample is flash-chromatographed (on silica Merck-60, eluant: dichloromethane-methanol 98:2 and 95:5).

NMR (DMSO-d$_6$, 400 MHz): δ2.75 (t, 2H, J 7.14 Hz, CH$_2$C), 3.02 (t, 2H, J 7.1 Hz, CH$_2$COO), 6.77 (d, 2H, J 8.7 Hz, ArH), 7.35 (d, 2H, J 8.55 Hz, ArH), 7.41 (t, 3H, J 7.12 Hz, ArH), 7.50 (d, 2H, J 7 Hz, ArH), 9.64 (broad s, exchangeable).

MS (EI, m/z): 309 (M)$^+$, 264 (M-COOH)$^+$, 121, 105, 77.

E. 5-Phenyl-4-(4-hydroxyphenyl)-2-oxazole propanoic acid methylester

A solution of the crude acid (5 g, 16.18 mmole) of Step D, in methanol (40 mL), containing a small amount of p-toluenesulfonic acid.H$_2$O (0.58 g) is refluxed for 2.5 hours. The methanol is evaporated and the residue is partitioned between ethyl acetate and 20% NaCl. The extracts are washed, dried (MgSO$_4$) and evaporated to yield a thick oil (ca. 4.8 g). The residue is flash-chromatographed (on silica Merck-60, preabsorbed in dichloromethane, eluted with a dichloromethane-ethyl acetate gradient from 90:10 to 75:25) to yield a white solid (3.56 g, 68%), m.p. 115°-116° C.

NMR (CDCl$_3$, 400 MHz): δ2.92 (t, 2H, J 7.4 Hz, CH$_2$C), 3.20 (t, 2H, J 7.4 Hz, CH$_2$COO), 3.71 (s, 3H, OCH$_3$), 6.74 (d, 2H, J 8.59 Hz, ArH), 7.26-7.36 (m, 3H, ArH), 7.40 (d, 2H, J 8.7 Hz, ArH), 7.54 (d, 2H, J 7.56 Hz, ArH).

MS (EI, m/z): 323 (M)$^+$, 264 (M-COOCH$_3$)$^+$, 105, 77 (b.p.).

F. 5-Phenyl-4-[4-(2-quinolinylmethoxy)phenyl]-2-oxazole propanoic acid methylester A mixture of the ester (2.46 g, 7.61 mmole) of Step E, powdered anhydrous K$_2$CO$_3$ (1.05 g, 7.60 mmole), 18-crown-6 (0.223 g, 0.843 mmole) and acetonitrile (33 mL, ex-sieves) is stirred at room temperature under nitrogen for 15 minutes. 2-Chloromethylquinoline (free base, freshly prepared from the hydrochloride salt, 1.35 g, 7.60 mmole) is added and the mixture is placed in an oil bath heated at 65° C. for 10 hours (N.B. A 10% excess of the chloromethylquinoline, 18-crown-6 and K$_2$CO$_3$ is added after 6 hours). The solvent is removed and the residue is partitioned between ethyl acetate and water. The extracts are washed (brine), dried (MgSO$_4$) and evaporated to yield a yellow solid. The crude product is flash chromatographed (on silica Merck-60, eluant: toluene and then toluene-methanol 97.5:2.5) to provide the title compound (3.5 g, quantitative yield).

NMR (CDCl$_3$, 400 MHz): δ2.90 (t, 2H, J ca. 7.2 Hz, CH$_2$C), 3.16 (t, 2H, J 7.2 Hz, CH$_2$COO), 3.72 (s, 3H, OCH$_3$), 5.41 (s, 2H, ArCH$_2$O), 7.02 (d, 2H, J 8.8 Hz, ArH), 7.29-7.36 (m, ca. 4H, ArH), 7.54-7.84 (m, ca. 6H, ArH), 7.83 (d, 1H, J 8.1 Hz, ArH), 8.08 (t, 1H, J 8.5 Hz, ArH), 8.19 (d, 1H, J 8.5 Hz, ArH).

MS (+FAB, m/z): 487 (M+Na)$^+$, 465 (M+H)$^+$.

G. 5-Phenyl-4-[4-(2-quinolinylmethoxy)phenyl]-2-oxazole propanoic acid

A solution of the ester (3.4 g, 7.32 mmole) of Step F, in dry tetrahydrofuran (37 mL) is treated dropwise under nitrogen with 1N-LiOH (21.98 mL, 3 equiv.) and stirred at room temperature for 3 hours (TLC, dichloromethane-methanol 97:3 or toluene-methanol 95:5). The solvent is evaporated, the residue is dissolved in water, neutralized in the cold with 10% acetic acid (to pH 5.5-6) and extracted with ethyl acetate. The extracts are washed with brine, dried (MgSO$_4$) and evaporated to yield a pale yellow solid (3.18 g, quantitative yield). The crude product is recrystallized from warm ethyl acetate (containing enough dichloromethane to obtain a clear solution) to yield a first crop of crystals (2.63 g, m.p. dec. 192°-194° C.). A second crop is obtained by concentrating the mother liquors (0.327 g, m.p. dec. 192°-193° C.). The combined yield is 85.8%.

IR (KBr, cm$^{-1}$): 1720 (CO).

NMR (DMSO-d$_6$, 400 MHz): δ2.76 (t, 2H, J 7 Hz, CH$_2$C), 3.03 (t, 2H, J 7 Hz, CH$_2$COO), 5.38 (s, 2H, ArCH$_2$O), 7.11 (d, 2H, J 8.8 Hz, ArH), 7.36-7.56 (m, 7H, ArH), 7.61 (t, 1H, ArH), 7.69 (d, 1H, J 8.5 Hz, ArH), 7.78 (t, 1H, ArH), 8.00 (t, J 7.9 Hz, 2H, ArH), 8.42 (d, 1H, J 8.5 Hz, ArH).

MS (EI or CI, m/z): 451 (M+H)$^+$, 310 (b.p.).

Analysis for: C$_{28}$H$_{22}$N$_2$O$_4$. Calculated: C, 74.65; H, 4.92; N, 6.22. Found: C, 74.20; H, 4.86; N, 6.00.

EXAMPLE 6

4-[4-[2-Naphthalenylmethoxy]phenyl]-5-phenyl-2-oxazole propanoic acid

A. 4-[4-[2-Naphthalenylmethoxy]phenyl]-5-phenyl-2-oxazole propanoic acid methylester A mixture of the hydroxyester (1.5 g, 4.6 mmole) of Example 5E, powdered anhydrous K$_2$CO$_3$ (0.636 g, 4.6 mmole), 18-crown-6 (0.123 g, 0.46 mmole) and acetonitrile (18 mL) is stirred at room temperature under nitrogen for 15 minutes. 2-Bromomethylnaphthalene (1.13 g, 5.1 mmole) is added and the mixture is placed in an oil bath heated at 70° C. for 8-9 hours (TLC, hexane-ethyl acetate 9:1 or dichloromethane-methanol 9:1). The solvent is evaporated and the residue dissolved in water and extracted with ethyl acetate. The extracts are washed and dried (MgSO$_4$). Removal of the solvent yields a tan solid (2.17 g, quantitative yield). A sample is recrystallized from methanol (containing enough dichloromethane to obtain a clear solution) by concentrating to small volume and cooling in an ice bath. The white solid is collected and dried overnight in vacuo, m.p. 134°-135° C.

IR (KBr, cm$^{-1}$): 1740 (CO).

NMR (CDCl$_3$-400 MHz): δ2.89 (t, 2H, J 7.5 Hz, CH$_2$C), 3.16 (t, 2H, J 7.5 Hz, CH$_2$COO), 3.71 (s, 3H, OCH$_3$), 5.2 (s, 2H, ArCH$_2$O), 7.00 (d, 2H, J 8.6 Hz, ArH), 7.25-7.35 (m, 3H, ArH), 7.46-7.58 (m, 7H, ArH), 7.8-7.9 (m, 4H, ArH).

MS (CI, m/z): 464 (M+H)$^+$, 324.

Analysis for: C$_{30}$H$_{25}$NO$_4$. Calculated: C, 77.73; H, 5.44; N, 3.02. Found: C, 77.44; H, 5.36; N, 3.03.

B.
4-[4-(2-Naphthalenylmethoxy)phenyl]-5-phenyl-2-oxazole propanoic acid A solution of the ester (1.49 g, 3.21 mmole) of Step A, in dry tetrahydrofuran (18 mL) containing 1N-LiOH (9.6 mL) is stirred under nitrogen overnight at room temperature (TLC, 75:25 hexane-ethyl acetate). The solvent is evaporated, the residue dissolved in water and acidified (to pH 5) with dilute HCl. The mixture is extracted with ethyl acetate, the extracts are dried (MgSO$_4$) and evaporated to yield the crude product (1.39 g, m.p. 145°-150° C.). For purification, it is dissolved in hot ethyl acetate (containing enough dichloromethane to obtain a clear solution), concentrated to half volume and precipitated with ether. The white solid melts at 151°-152° C. (1.07 g, 58%).

IR (KBr, cm$^{-1}$): 1720 (CO).

NMR (DMSO-d$_6$, 400 MHz): δ2.78 (t, 2H, CH$_2$C), 3.03 (t, 2H, J 7 Hz, CH$_2$COO), 5.29 (s, 2H, ArCH$_2$O), 7.10 (d, 2H, J 8.9 Hz, ArH), 7.34-7.60 (m, 10H, ArH), 7.90-8.00 (m, 4H, ArH), 12.28 (s, 1H, COOH).

MS (EI, m/z): 450 (M+H)$^+$, 310.

Analysis for: C$_{29}$H$_{23}$NO$_4$. Calculated: C, 77.48; H, 5.15; N, 3.11. Found: C, 76.40; H, 5.16; N, 3.04.

EXAMPLE 7
4-[4-[(1-Methyl-1H-benzimidazol-2-yl)methoxy]-phenyl]-5-phenyl-2-oxazole propanoic acid

A.
4-[4-[(1-Methyl-1H-benzimidazol-2-yl)methoxy]-phenyl]-5-phenyl-2-oxazole propanoic acid methylester A mixture of the ester (0.5 g, 1.55 mmole) of Example 5E, powdered anhydrous K$_2$CO$_3$ (0.214 g, 1.55 mmole), 18-crown-6 (0.0416 g, 0.155 mmole) and acetonitrile (6 mL) is stirred under nitrogen at room temperature for 15 minutes. 2-Chloromethyl-1-methylbenzimidazole (0.307 g, 1.7 mmole) is added and the mixture is placed in an oil bath heated at 65°-70° C. for 4 hours (TLC, dichloromethane-ethyl acetate 9:1, iodine visualization). A 10% excess of K$_2$CO$_3$, 2-chloromethyl-1-methyl-benzimidazole and 18-crown-6 is added at this point and the heating continued for another 10 hours. The solvent is evaporated, the residue dissolved in water and extracted with ethyl acetate. The extracts are washed, dried (MgSO$_4$) and evaporated to dryness. The residue (1.64 g) is purified by flash-chromatography (on silica Merck-60, preabsorbed in dichloromethane containing a small amount of methanol, eluted with dichloromethane-ethyl acetate 8:2) to yield 1.03 g (71.2%) of a light yellow solid, m.p. 142°-144° C. (dec).

NMR (CDCl$_3$, 400 MHz): δ2.87 (t, 2H, J 7.1 Hz, CH$_2$C), 3.16 (t, 2H, J 7.8 Hz, CH$_2$COO), 3.72 (s, 3H, COOCH$_3$), 3.90 (s, 3H, NCH$_3$), 5.41 (s, 2H, ArCH$_2$O), 7.07 (d, 2H, J 8.8 Hz, ArH), 7.25-7.40 (m, 7H, ArH), 7.5-7.6 (m, 3H, ArH), 7.78 (d, 1H, ArH).

MS (+CI, m/z): 468 (M+H)$^+$, 324, 293, 147.

B.
4-[4-[(1-Methyl-1H-benzimidazol-2-yl)methoxy]-5-phenyl-2-oxazole propanoic acid A solution of the ester (1 g, 2.14 mmole) of Step A, in tetrahydrofuran (13 mL) containing 1N-LiOH (6.42 mL) is stirred under nitrogen at room temperature for 1 hour (TLC, dichloromethane-ethanol 9:1). The solvent is evaporated, water added and the pH adjusted to 6.5 with 10% acetic acid. The light yellow precipitate is collected, washed with water and dried in vacuo. It is redissolved in hot ethyl acetate (containing enough methanol to obtain a clear solution), concentrated to a smaller volume and cooled in an ice bath. The crystals are collected and dried (0.642 g, 66.2%, m.p. 222°-224° C.).

NMR (DMSO-d$_6$, 400 MHz): δ2.76 (t, 2H, J 7 Hz, CH$_2$C), 3.03 (t, 2H, J 7 Hz, CH$_2$COO), 3.86 (s, 3H, NCH$_3$), 5.43 (s, 2H, ArCH$_2$O), 7.14-7.66 (m, 13H, ArH).

MS (CI, m/z): 454 (M+H)$^+$, 147 (b.p.).

Analysis for: C$_{27}$H$_{23}$N$_3$O$_4$. Calculated: C, 71.51; H, 5.11; N, 9.27. Found: C, 71.62; H, 5.17; N, 9.40.

EXAMPLE 8
N-Hydroxy-N-methyl-2-fluoro-4'-(2-quinolinylmethoxy)-[1,1'-biphenyl]-4-acetamide To a solution of the acid of Example 2 (1.0 g, 2.58 mmol) in methylene chloride (20 ml) containing dimethylformamide (0.2 ml), 2.58 mmol) at 0° C. is added oxalyl chloride (0.506 ml, 5.80 mmol), dropwise. After the reaction mixture is stirred for 1 hour, it is added dropwise to a solution of N-methylhydroxylamine hydrochloride (0.861 g, 10.32 mmol) in triethylamine (1.87 ml, 13.41 mmol), tetrahydrofuran (10 ml) and water (10 ml) at 0° C. After overnight stirring, the reaction mixture is poured into 2N HCl, the ensuing solid is collected and recrystallized from ethanol. The crystals are then flash chromatographed eluting with ethyl acetate-hexane (3:2) followed by ethyl acetate-ethanol (99:1). The material at this point is still contaminated with a minor impurity which is removed by conversion of the material to the hydrochloride salt, followed by washing with ethyl acetate, basification and final extraction with ethyl acetate to afford white crystals, m.p. 153°-155° C.

Analysis for: C$_{25}$H$_{21}$N$_2$O$_3$F. Calculated: C, 72.10; H, 5.08; N, 6.73. Found: C; 71.95; H, 5.07; N, 6.39.

EXAMPLE 9
2-Fluoro-4'-(2-quinolinylmethoxy)[1,1'-biphenyl]-4-acetic acid, 2-amino-2-hydroxymethyl-1,3-propane diol A solution of the compound of Example 2 (3.17 g, 8.2 mmole) and 2-amino-2-hydroxymethyl-1,3-propane diol [TRIS, 0.99 g, 8.2 mmole] in 60 mL of methanol is concentrated to a syrup. Following dilution with ethylacetate (250 mL), the crystalline precipitate is collected and dried to give 3.18 g of the title salt. The product is micronized to a fine white powder, m.p. 168°-169° C. (77.5% yield).

Analysis for: C$_{28}$H$_{29}$FN$_2$O$_6$. Calculated: C, 66.13; H, 5.75; N, 5.51. Found: C, 65.75; H, 5.79; N, 5.49.

EXAMPLE 10
5-Phenyl-4-[4-quinolinylmethoxy)-phenyl]-2-oxazole propionic acid, 2-amino-2-hydroxymethyl-1,3-propane diol To a solution of the compound of Example 5 (0.359 g, 0.796 mmole) in boiling ethanol (35 mL) is added 2-amino-2-hydroxymethyl-1,3-propane diol [TRIS, 0.0965 g, 0.796 mmole] in 0.5 mL of water. After two hours, the mixture is refrigerated. The crystalline precipitate is collected and dried to give 0.396 g of the title salt, m.p. 170°-171° C.

Analysis for: C$_{32}$H$_{33}$N$_3$O$_7$. Calculated: C, 67.00; H, 5.75; N, 7.32. Found: C, 66.68; H, 5.77; N, 7.31.

EXAMPLE 11

4'-(2-Benzothiazolylmethoxy)-4-diphenylacetic acid, ethyl ester

A. 4'-Hydroxy-4-diphenylacetic acid, ethyl ester

A solution containing 4'-hydroxy-4-diphenylacetic acid (6.7 g, 28.0 mmol), absolute ethanol (300 ml) and concentrated sulfuric acid (5 ml) is refluxed for 2 hours. The reaction mixture is cooled to room temperature, concentrated under reduced pressure, diluted with water (200 ml) and extracted with ethyl acetate (200 ml; 3 times). The combined ethyl acetate extract is washed with 1N sodium hydroxide (200 ml), water (200 ml) and brine (200 ml), is dried over anhydrous magnesium sulfate and is concentrated under reduced pressure to afford 6.9 g of crude solids. The solids are purified by chromatography (silica gel; 30% ethyl acetate in hexane) to give 6.7 g (95.0%) of white crystalline product, m.p. 125°–127° C.

Analysis for: $C_{16}H_{16}O_3$. Calculated: C, 74.98; H, 6.29. Found: C, 74.62; H, 6.22.

B. 4'-(2-Benzothiazolylmethoxy)-4-diphenylacetic acid, ethyl ester

A slurry of 4'-hydroxy-4-diphenylacetic acid, ethyl ester (6.7 g, 26.0 mmol, Part A.) and cesium carbonate (9.0 g, 28.0 mmol) in dimethylsulfoxide (150 ml) is stirred at room temperature. After 30 minutes, 2-(chloromethyl)-benzothiazole (4.2 g, 27.0 mmol) is added and the mixture is stirred for 18 hours. The reaction mixture is poured into ice-water (200 ml) and is extracted with ethyl acetate (300 ml, 3 times). The combined ethyl acetate extract is washed sequentially with 0.1N sodium hydroxide (200 ml), water (200 ml) and brine (200 ml), is dried over anhydrous magnesium sulfate, and concentrated under reduced pressure to give 8.0 g of crude solids. The solids are purified by chromatography (silica gel, 30% ethyl acetate in hexane) to afford 4.0 g (39.2%) of white crystalline product, m.p. 133°–134° C.

Analysis for: $C_{24}H_{21}NO_3S$. Calculated: C, 71.44; H, 5.25; N, 3.47. Found: C, 71.36; H, 5.25; N, 3.35.

EXAMPLE 12

4'-(Benzothiazolylmethoxyl)-4-diphenylacetic acid

A mixture of 4'-(benzothiazolylmethoxy)-diphenylacetic acid, ethyl ester (4.0 g, 10.0 mmol), 1N sodium hydroxide (15 ml, 15.0 mmol), methanol (200 ml) and tetrahydrofuran (200 ml) is refluxed for 18 hours. The reaction mixture is cooled, concentrated under reduced pressure, is diluted with water (500 ml) and with stirring, is acidified with 2N hydrochloric acid. After stirring for two hours, the product is collected by filtration and after vacuum drying, 3.8 g (99%) of solids is obtained. A portion of this material (0.5 g) is recrystallized from acetic acid, m.p. 208°–209° C.

Analysis for: $C_{22}H_{17}NO_3S$. Calculated: C, 70.38; H, 4.56; N, 3.73. Found: C, 70.04; H 4.56; N, 3.72.

EXAMPLE 13

4'-(Benzothiazolylmethoxy)-4-diphenyl-N-hydroxy-N-methyl-acetamide

A mixture of 4'-(benzothiazolylmethoxy)-4-diphenylacetic acid (1.0 g, 3.0 mmol), methylene chloride (50 ml) and dimethylacetamide (0.21 ml) is cooled to 5° C. and with stirring, a solution of oxalyl chloride (0.6 ml) in methylene chloride (10 ml) is added slowly. After stirring at room temperature for 30 minutes, the reaction mixture is poured into a solution containing tetrahydrofuran (13 ml), water (1.2 ml), triethylamine (2.0 ml) and N-methylhydroxylamine hydrochloride (1.0 g, 12.0 mmol). After stirring for 1 hour the reaction mixture is diluted with methylene chloride (100 ml), is poured into 2N hydrochloric acid (100 ml) and is extracted. The aqueous layer is washed again with methylene chloride (100 ml). The combined methylene chloride extract is washed with water (100 ml) and brine (100 ml), is dried over anhydrous magnesium sulfate and is concentrated under reduced pressure to afford 1.0 g of crude solid product. The solids are recrystallized from acetonitrile to give 0.6 g (60%) of a yellowish-colored crystalline solid, m.p. 176°–179° C.

Analysis for: $C_{23}H_{20}N_2O_3S$. Calculated: C, 68.30; H, 4.98; N, 6.93. Found: C, 68.70; H, 4.89; N, 6.62.

EXAMPLE 14

The compounds 5- and 12-hydroxyeicosatetraenoic acid (5-HETE and 12-HETE) and $LTB_4$ are early arachidonic acid oxidation products in the lipoxygenase cascade, which have been shown to mediate several aspects of inflammatory and allergic response. This is especially true with respect to 5,12-diHETE, which is also denoted as $LTB_4$ [see Ford-Hitchinson, *J. Roy. Soc. Med.*, 74, 831 (1981)]. Compounds which inhibit the $PLA_2$-mediated release of arachidonic acid thereby effectively prevent the oxidation of arachidonic acid to the various leukotriene products via the lipoxygenase cascade. Accordingly, the specificity of action of $PLA_2$ inhibitors can be determined by the activity of test compounds in this assay, which measures the ability of compounds to inhibit the synthesis of $LTB_4$ by rat glycogen-elicited polymorphonuclear leukocytes (PMN) in the presence of exogenous substrate.

The assay is carried out as follows:

Rat polymorphonuclear leukocytes (PMNs) are obtained from female Wistar rats (150-200 g) which receive an injection of 6% glycogen (10 ml i.p.). Rats are sacrificed 18–24 hours post injection by $CO_2$ asphyxiation and the elicited cells are harvested by peritoneal lavage using physiological saline (0.9% NaCl). The exudate is centrifuged at 400 xg for 10 minutes. The supernatant fluid is discarded and the cell pellet is resuspended to a concentration of $2.0 \times 10^7$ cells/mL in HBSS containing $Ca^{++}$ and $Mg^{++}$ and 10 $\mu$M L-cysteine.

To 1 mL aliquots of cell suspension, test drugs or vehicle are added, then preincubated at 37° C. for 10 minutes. A23187 (1 $\mu$M), [$^3$H]-AA (3.0 $\mu$Ci/mL) and unlabeled AA (1 $\mu$M) are then added and the samples are further incubated for 10 minutes. The reaction is terminated by centrifugation and pelleting cells. Supernatants are then analyzed by HPLC analysis on a 15 cm $\times$ 4.6 mm ID supelcosil LC-18 (Supelco)(3M) column, using a two solvent system at a flow rate of 1.4 mL total flow as follows:

Solvent A: 70:30 17.4 mM $H_3PO_4$:$CH_3CN$
Solvent B: $CH_3CN$
Gradient: (system is equilibrated with Solvent A)

| Time | Percent A | Percent B |
| --- | --- | --- |
| 0 | 100 | 0 |
| 15.0 | 100 | 0 |
| 20.0 | 65 | 35 |
| 40.0 | 65 | 35 |

-continued

| Time | Percent A | Percent B |
|------|-----------|-----------|
| 42.0 | 10 | 90 |
| 50.0 | 10 | 90 |
| 50.1 | 100 | 0 |

Percent solvent changes are accomplished in a linear fashion.

Injections: 140 μL of each supernatant is injected directly onto column and $^3$H arachidonic acid metabolites are monitored using an on-line radioactivity detector (Ramona, IN/US, Fairfield, N.J.).

Standards: $10^4$–$2.0 \times 10^4$ dpm of eicosanoids of interest are injected in 90 μL EtOH cocktail.

Co-chromatography with standard [$^3$H] leukotriene B$_4$ (LTB$_4$) in medium of stimulated PMN exposed to drug is compared to that found in medium of stimulated cells exposed to no drug, generating percent inhibition.

Results are expressed as percent inhibition at a given compound dose or as an IC$_{50}$ value.

Testing compounds of the invention in this assay gave the following results:

TABLE I

| Compound of Example No. | % Inhibition |
|---|---|
| ketoprofen | −50* (at 10 μM) |
| 1 | 95 (at 0.5 μM) |
| 2 | 91 (at 0.5 μM) |
| 3 | 87 (at 10 μM) |
|  | 38 (at 0.5 μM) |
| 4 | 8 (at 10 μM) |
| 5 | 96 (at 10 μM) |
| 6 | 95 (at 10 μM) |
|  | 81 (at 0.5 μM) |
| 6A | 94 (at 10 μM) |
|  | 63 (at 0.5 μM) |
| 7 | 85 (at 10 μM) |

*a negative value denotes potentiation of cyclooxygenase (PGE$_2$ synthesis)

EXAMPLE 15

The procedure of Example 14 is also employed for the determination of the extent to which compounds of the invention inhibit the synthesis of the arachidonic acid cyclooxygenase oxidation product PGE$_2$.

In this assay, the procedure of Example 14 is carried out as described. However, in order to determine cyclooxygenase activity, the samples are cochromatographed with authentic reference [$^3$H]-PGE$_2$.

The results are calculated as in Example 14 and presented below:

TABLE II

| Compound of Example No. | % Inhibition |
|---|---|
| ketoprofen | 87 (at 10 μM) |
| 1 | −13* (at 0.5 μM) |
| 2 | −22* (at 0.5 μM) |
| 3 | 8 (at 10 μM) |
|  | −8* (at 0.5 μM) |
| 4 | −31* (at 10 μM) |
| 5 | −275* (at 10 μM) |
| 6 | −191* (at 10 μM) |
|  | −12* (at 0.5 μM) |
| 6A | −79* (at 10 μM) |
|  | −29* (at 0.5 μM) |
| 7 | −268* (at 10 μM) |

*Negative values denote a potentiation of cyclooxygenase (PGE$_2$ synthesis).

EXAMPLE 16

The compounds of the invention are tested in an in vitro isolated phospholipase A$_2$ assay to determine the ability of the test compounds to inhibit the release of arachidonic acid from an arachidonic acid-containing substrate by the action of phospholipase A$_2$ enzyme from human and non-human sources.

This assay is carried out as follows:

Into a 15 mL polypropylene tube are added the following:

| Agent | Volume, μL | Final Conc. |
|---|---|---|
| $^3$H-AA E. coli substrate[1] | 25 | 5 nmoles PL |
| CaCl$_2$ (0.1M)[2] | 5 | 5 mM |
| Tris-HCl (0.5M) pH 7.5[3] | 20 | 100 mM |
| Water[4] | 25 |  |
| Drug/vehicle[5] | 1 | 50 μM |
| PLA$_2$ | 25 | Volume yielding 12% hydrolysis in 10 min. |
|  | 100 |  |

*pre-incubate at room temperature 30 min prior to substrate addition.
[1]Prepared by adding 2 mL deionized and distilled water to 2 mL $^3$H-arachidonate labeled E. coli (lower count), to which is added 1 mL of $^3$H-arachidonate labeled E. coli (higher count) to yield a total of 5 m substrate (containing 1000 nmoles phospholipid).
[2]Stock 0.1 m CaCl$_2$, required for enzyme activity.
[3]Stock 0.5 m Trisma-Base. Stock 0.5M Trisma-HCl. Adjust pH to 7.5 (optimum for enzyme).
[4]Deionized and distilled water.
[5]Stock 10 mM prepared in dimethyl sulfoxide. Make 1:2 dilution with dimethyl sulfoxide and add 1 μL to 100 μL assay tube.
[6]Two human PLA$_2$ enzymes are used:
a) Semi-purified human platelet acid extract PLA$_2$ (in 10 mM sodium acetate buffer, pH 4.5). Remove protein precipitate by centrifugation at about 2200 rpm for 10 minutes.
b) Purified human synovial fluid.

Incubate the 100 μL reaction mixture for 10 minutes at 37° C. in a shaking water bath. The reaction is terminated by the addition of 2 mL tetrahydrofuran, followed by vortexing. NH$_2$ columns (100 μg/mL—Analytichem International) are conditioned with 0.5 mL tetrahydrofuran followed by 0.5 mL tetrahydrofuran/water (2 mL:0.1 mL, v/v).

The sample is loaded onto the columns and slowly drawn through them. The hydrolyzed arachidonic acid retained in the columns is eluted therefrom with 1 mL tetrahydrofuran/glacial acetic acid (2%). The arachidonic acid is transferred to scintillation vials and quantitated by β-counting analysis. A "total counts" sample is prepared by pipetting 25 μL $^3$H-arachidonate E. coli directly into a scintillation vial to which is added 1 mL tetrahydrofuran. 10 mL aquasol (scintillation cocktail) is added to all samples.

Calculations:

$$\% \text{ hydrolysis} = \frac{[3H]AA \text{ dpm (sample)} - [3H]AA \text{ dpm (nonspecific hydrolysis)}}{\text{total counts dpm}} \times 100$$

$$\% \text{ change} = \frac{\text{vehicle dpm} - \text{drug dpm}}{\text{vehicle dpm}} \times 100$$

Activity of Standard Drugs:

| Drug | IC$_{50}$ (μM) Human Platelet PLA$_2$ | Human Synovial PLA$_2$ |
|---|---|---|
| Arachidonic Acid | 8.6 | 3.2 |
| Monoalide | 25.2 | 0.14 |

When tested in this assay, the compounds of the invention gave the following results:

TABLE III

| Compound of Example No. | % Inhibition at 10 μM HSF* |
|---|---|
| ketoprofen | −16.9** |
| 3 | 25.5 |
| 4 | 15.1 |

*human synovial fluid
**negative values denote a potentiation of HSF

EXAMPLE 17

The compounds of the invention are evaluated for their ability to inhibit the lipoxygenase and/or cyclooxygenase pathways of arachidonic acid metabolism in the in vivo murine zymosan peritonitis assay.

This assay is carried out as follows:

Male CD-1 mice (8 weeks old) are placed in plastic boxes in groups of six. Animals are injected with 1 mL i.p. of either 1% zymosan in pyrogen free 0.9% saline or saline (unstimulated control). Compounds are dosed orally 1 hour prior to zymosan injection. Twenty minutes after zymosan injection, the mice are asphyxiated by $CO_2$ inhalation and the peritoneal cavity is lavaged with 2 mL ice cold Hanks Balanced Salt Solution (HBSS) without $CaCl_2$, $MgSO_4 \cdot 7H_2O$ and $MgCl_2 \cdot 6H_2O$. Peritoneal lavage fluid from each mouse is removed by syringe and placed in 5 mL plastic test tubes put on ice and volume is noted. Preparation of samples for evaluation by ELISA is as follows: Samples are centrifuged at 800 xg for 15 minutes; 1 mL of the supernatant is added to 8 mL ice cold methanol and kept at −70° C. overnight to precipitate protein; and samples are then centrifuged at 800 xg for 15 minutes, followed by a drying procedure in a Savant speed vac concentrator. The samples are reconstituted with 1 mL ice cold ELISA buffer and stored at −70° C. until assayed. The assay for eicosanoids ($LTC_4$ and 6-keto-$PGF_{1\alpha}$) is performed according to conventional ELISA procedures.

Compounds to be tested orally are suspended in 0.5% Tween 80. Compounds to be tested intraperitoneally are suspended in 0.5% methylcellulose in 0.9% saline.

The total metabolite level in lavage fluid/mouse is calculated and the significance is determined by a one-way analysis of variance with LSD comparisons to control ($p \leq 0.05$). Drug effects are expressed as a percent change from control values.

The activity of standard drugs in this assay is as follows:

| | $ED_{50}$ mg/kg p.o. | |
|---|---|---|
| Compound | $LTC_4$ | 6-keto-$PGF_{1\alpha}$/$TxB_2$ |
| BW755C | <10 | 22.0 |
| Phenidone | 24.0 | <30.0 |
| Indomethacin | Not Active | 0.126 |
| Ibuprofen | Not Active | 7.0 |

When tested in this assay a compound of the invention and the anti-inflammatory compound etodolac gave the following results:

TABLE IV

| Compound of Example No. | Dose mg/kg | % Inhibition $LTC_4$ | 6-keto-PGF |
|---|---|---|---|
| 5 | 10 (i.p.)* | 86 | −27** |

*intraperitoneally administered
**negative values denote potentiation

The results show that the compound of the invention exerts a potent inhibitory effect on the lipoxygenase pathway but not on the cyclooxygenase pathway.

EXAMPLE 18

The compounds of the invention are further tested in the reverse passive Arthus pleurisy assay to evaluate their effectiveness in inflammatory mediator release and/or the fluid and cellular phases of an inflammatory response.

This assay is carried out as follows:

A reverse passive Arthus reaction is induced in the pleural cavity of male Lewis rats (150-200 g; fasted overnight prior to use) by the intravenous administration of bovine serum albumin (BSA; 4 mg/0.2 ml) followed by 30 minutes later by the injection of rabbit anti-BSA (1 mg/0.2 ml; lyophilized IgG fraction; Organon Teknika, West Chester, Pa.) into the right pleural space under halothane anesthesia. Drugs or vehicle (0.5% Tween-80) control are administered orally in a volume of 1 ml/100 g body weight at 1 hour prior to the anti-BSA. Animals are sacrificed at either the time of peak eicosanoid production (i.e. 5 minutes after anti-BSA for immunoreactive $TxB_2$ 10 minutes for immunoreactive $LTB_4$, 20 minutes for immunoreactive $LTC_4$) or at the time of peak neutrophil infiltration (4 hours after anti-BSA) by $CO_2$ inhalation. The pleural cavity is then exposed, the fluid exudate removed by gentle vacuum aspiration and the volume of exudate is recorded. For the determination of cellular infiltration, the pleural cavity is rinsed with 3 ml of 0.1% EDTA in sterile saline, and the recovered wash is pooled with the exudate. Cell number is determined on a model ZBI Coulter counter. For determination of eicosanoid production, undiluted pleural exudate is microfuged and the supernatant is extracted with ethanol (8-10 times volume). Extracts are either stored at −20° C., or are evaporated to dryness under a stream of $N_2$ and reconstituted in radioimmunoassay (RIA) buffer.

Eicosanoids are quantitated by RIA according to the procedure specified by the RIA kit manufacturer (Advanced Magnetics, Cambridge, Mass.). Briefly, 100 μl of $^3H$-labeled eicosanoid and 100 μl of specific antibody are sequentially added to 100 μl of extracted pleural exudate in BGG -phosphate buffer which contains 0.01M phosphate, 0.1% bovine gamma globulin and 0.1% sodium azide at pH 7.0. Antibody-bound eicosanoid is separated from unbound eicosanoid by the addition of 750 μl of dextran (0.4%)-coated charcoal (0.4% Norit A) containing 0.1% sodium azide. The mixture is centrifuged at 2000 RPM at 5° C. for 15 minutes to pellet the charcoal and adsorbed unbound eicosanoid. Antibody-bound labeled eicosanoid is quantitated by counting in a liquid scintillation counter, and is correlated to concentration by a standard curve.

Inflammatory cells are expressed as $10^6$ cells/ml, pleural exudate is expressed as ml of fluid, and the amount of eicosanoids in the pleural cavity is expressed as ng/ml of exudate. Mean±S.E.M. is determined for each group. Percent inhibition (% I) of cell number, exudate volume and eicosanoid production is calculated for vehicle-treated control groups, and the responses in drug-treated rats are then expressed as the mean % I of the control. The $ED_{30}$ or $ED_{50}$ with 95% confidence limits is calculated by the method of Litchfield and Wilcoxon, *J. Pharmac. Exp. Ther.*, 96, 99–113 (1949).

The activity of standard drugs in this assay is as follows:

A. Inflammatory Mediator Release:

| Antiinflammatory Drug | Class | $ED_{50}$ (mg/kg p.o.) | |
|---|---|---|---|
| | | $TxB_2$ | $LTB_4$ |
| Indomethacin | NSAID; CO inhibitor | 0.16 | 12% Inh (4 mg/kg) |
| Naproxen | | 0.24 | 0% Inh (4 mg/kg) |
| Diclofenac | | 6.0 | 0% Inh (10 mg/kg) |
| Ketoprofen | | 0.18 | 35% Inh (10 mg/kg) |
| Wy-50,295-A | LO Inhibitor | 0% Inh (75 mg/kg) | |
| BW540C | Mixed CO/LO Inhibitor | 19 | 30 |
| BW755C | | 18 | 23 |
| Phenidone | | 69 | 10 |

B. Pleural Inflammation:

| Antiinflammatory Drug | Class | $ED_{30}$ (mg/kg p.o.) | |
|---|---|---|---|
| | | Fluid Exudation | Cellular Influx |
| Indomethacin | NSAID; CO inhibitor | 2.5 | 19% Inh (8 mg/kg) |
| Naproxen | | 3.9 | 29% Inh (8 mg/kg) |
| Piroxicam | | 1.0 | 3.0 |
| BW755C | Mixed CO/LO inhibitor | 14 | 28 |
| Phenidone | | .21 | 23 |
| Dexamethasone | Steroid | 0.05 | 0.13 |

When tested in this assay, the compounds of the invention gave the following results:

TABLE VI

| Compound of Example No. | % Inhibition of $LTB_4$ Synthesis | $ED_{50}$ (mg/kg) |
|---|---|---|
| 2 | 34 | |
| 9 | | 0.8 |
| 10 | 65 | |

The results show that the compounds tested have a very significant effect in inhibiting the release of inflammatory mediators and in inhibiting the fluid and cellular phases of the inflammatory response.

What is claimed is:

1. A compound having the formula $A(CH_2)_nO$—B wherein
A is

[quinoline structure]

n is 1–2;
B is

[biphenyl ketone with CHCOOR⁵ structure]

[biphenyl with R⁶, R⁷ structure]

[isoxazole with CH(CH₂)ₘCOOR⁵ structure] or

[isoxazole with CH(CH₂)ₘCOOR⁵ structure]

wherein
$R^4$ and $R^5$ are each, independently, hydrogen or lower alkyl;
$R^6$ is hydrogen, halo or nitro;

$R^7$ is $-\overset{O}{\underset{\|}{C}}-R^8$, $-\overset{R^4}{\underset{|}{C}}HCOOR^5$, $-\overset{R^4}{\underset{|}{C}}HN(OH)\overset{O}{\underset{\|}{C}}NH_2$, $-\overset{R^4}{\underset{|}{C}}HNH\overset{O}{\underset{\|}{C}}NR^4$, or $-\overset{R^4}{\underset{|}{C}}H\overset{O}{\underset{\|}{C}}N(OH)R^8$;
$\quad\quad\quad\underset{OH}{|}$ $R^8$ is lower alkyl;
m is 0–3;
and the pharmacologically acceptable salts thereof.

2. The compound of claim 1, having the name 1-[2-nitro-4'-(2-quinolinylmethoxy)-[1,1'-biphenyl]4-yl]ethanone.

3. The compound of claim 1, having the name 2-fluoro-4'-(2-quinolinylmethoxy-[1,1'-biphenyl]-4-acetic acid.

4. The compound of claim 1, having the name 3-[4-(2-quinolinylmethoxy)benzoyl]benzene acetic acid.

5. The compound of claim 1, having the name 5-phenyl-4-[4-(2-quinolinylmethoxy)-phenyl]-2-oxazole propanoic acid.

6. The compound of claim 1, having the name N-hydroxy-N-methyl-2-fluoro-4'-(2-quinolinylmethoxy)-[1,1'-biphenyl]-4-acetamide.

7. The compound of claim 1, having the name 2-fluoro-4'-(2-quinolinylmethoxy)[1,1'-biphenyl]-4-acetic acid, 2-amino-2-hydroxymethyl-1,3-propane diol.

8. The compound of claim 1, having the name 5-phenyl-4-[4-quinolinylmethoxy)-phenyl]-2-oxazole propionic acid, 2-amino-2-hydroxymethyl-1,3-propane diol.

* * * * *